(12) United States Patent
Kathirgamanathan et al.

(10) Patent No.: US 7,462,404 B2
(45) Date of Patent: Dec. 9, 2008

(54) ELECTROLUMINESCENT BORON COMPLEXES

(75) Inventors: Poopathy Kathirgamanathan, North Harrow (GB); Matthew Samuel Kirkham, Twickenham (GB); Alexander Kit Lay, Reading (GB); Subramaniam Ganeshamurugan, London (GB); Gnanamoly Paramaswara, London (GB); Muttulingam Kumaraverl, Middlesex (GB); Arumugam Partheepan, Surrey (GB); Selvadurai Selvaranjan, Surrey (GB); Juan Antipan-Lara, London (GB); Richard Price, London (GB); Sivagnanasundram Surendrakumar, Middlesex (GB)

(73) Assignee: Merck Patent GmbH, Darmstadt (DE)

( * ) Notice: Subject to any disclaimer, the term of this patent is extended or adjusted under 35 U.S.C. 154(b) by 460 days.

(21) Appl. No.: 10/549,430

(22) PCT Filed: Mar. 12, 2004

(86) PCT No.: PCT/GB2004/001079

§ 371 (c)(1),
(2), (4) Date: Sep. 15, 2005

(87) PCT Pub. No.: WO2004/084325

PCT Pub. Date: Sep. 30, 2004

(65) Prior Publication Data

US 2007/0042219 A1    Feb. 22, 2007

(30) Foreign Application Priority Data

Mar. 15, 2003  (GB)  ................................ 0306097.7

(51) Int. Cl.
*H01L 51/54* (2006.01)
*C09K 11/06* (2006.01)

(52) U.S. Cl. .................. 428/690; 428/917; 548/110; 546/13; 313/504; 313/506; 257/E51.041; 544/180; 544/229

(58) Field of Classification Search ................ 313/504, 313/506; 257/E51.041, E51.047, E51.05, 257/E51.051; 544/180, 229; 546/13; 548/110
See application file for complete search history.

(56) References Cited

U.S. PATENT DOCUMENTS 6,287,713 B1    9/2001   Heuer et al.
6,368,731 B1    4/2002   Heuer et al.

OTHER PUBLICATIONS

Wu et al., Organometallics, (2003), vol. 22, p. 4938-4946.*
Cheng, Chung-Chih et al. "Syntheses and remarkable photophysical properties of 5-(2-pyridyl) pyrazolate boron complexes; photo-induced electron transfer" Chemical Communications Oct. 3, 2003.
Liu Y et al. "Highly efficient white organic electroluminescence from a double-layer device based on a boron hydroxyphenylpyridine complex" Angewandte Chemie, Int'l Ed. Jan. 4, 2002.
Li et al. "A mixed pyridine-phenol boron complex as an organic electroluminescent material" Chemical Communications No. 16 2000.
Wu Q et al. "Synthesis, structure and electroluminescence of BR2q (R=Et, Ph, 2-naphthyl and q+8-hydroxyauinolato)" Chemistry of Materials, vol. 12, No. 1, Jan. 2000.

* cited by examiner

*Primary Examiner*—Dawn Garrett
(74) *Attorney, Agent, or Firm*—David Silverstein; Andover-IP-Law

(57) ABSTRACT

Novel boron complexes are blue emissive electroluminescent compounds.

20 Claims, 27 Drawing Sheets

Alq

Bebq

BAlq1

ZnPBO

ZnPBT

DTVb1 or

α-NPB

TPD mTADATA

ELECTROLUMINESCENT BORON COMPLEXES

The present invention relates to electroluminescent materials and to electroluminescent devices.

Materials which emit light when an electric current is passed through them are well known and used in a wide range of display applications. Liquid crystal devices and devices which are based on inorganic semiconductor systems are widely used. However these suffer from the disadvantages of high energy consumption, high cost of manufacture, low quantum efficiency and the inability to make flat panel displays.

Organic polymers have been proposed as useful in electroluminescent devices, but it is not possible to obtain pure colors; they are expensive to make and have a relatively low efficiency.

Another compound which has been proposed is aluminium quinolate, but this requires dopants to be used to obtain a range of colors and has a relatively low efficiency.

Patent application WO98/58037 describes a range of lanthanide and transition metal complexes which can be used in electroluminescent devices which have improved properties and give better results. Patent Applications PCT/GB98/01773, PCT/GB99/03619, PCT/GB99/04030, PCT/GB99/04024, PCT/GB99/04028, PCT/GB00/00268 describe electroluminescent complexes, structures and devices using rare earth chelates.

U.S. Pat. No. 5,128,587 discloses an electroluminescent device which consists of an organometallic complex of rare earth elements of the lanthanide series sandwiched between a transparent electrode of high work function and a second electrode of low work function with a hole conducting layer interposed between the electroluminescent layer and the transparent high work function electrode and an electron conducting layer interposed between the electroluminescent layer and the electron injecting low work function cathode. The hole conducting layer and the electron conducting layer are required to improve the working and the efficiency of the device. The hole transporting layer serves to transport holes and to block the electrons, thus preventing electrons from moving into the electrode without recombining with holes. The recombination of carriers therefore mainly takes place in the emitter layer.

U.S. Pat. Nos. 6,287,713 and 6,368,731 the contents of which are incorporated by reference disclose electroluminescent compounds which are complexes of boron with 8-aminoquinolate derivatives.

We have now invented novel electroluminescent boron complexes.

Figure 1:
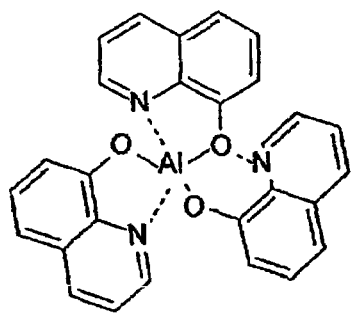
FIGS. 1 and 2 illustrate chemical formulae for electron injecting materials in accordance with this invention.
Figure 1:
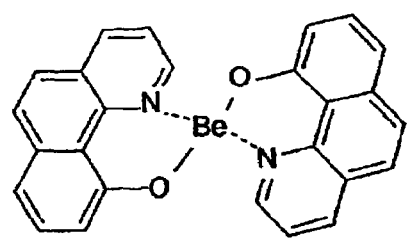
Figure 1:
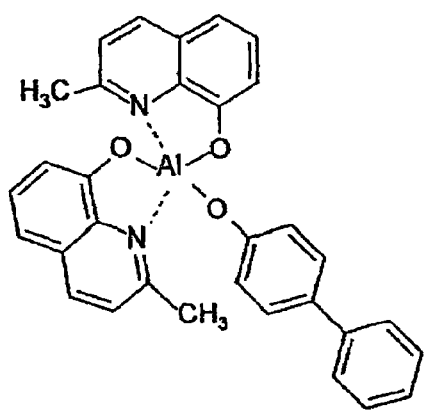
Figure 1:
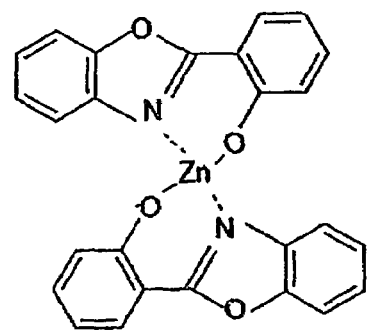
Figure 1:
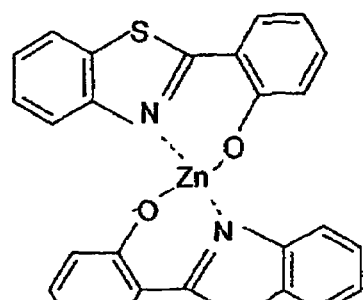
Figure 1:
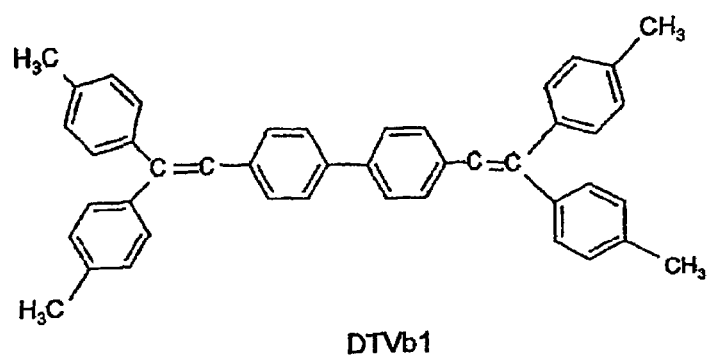

According to the invention there is provided a boron compound of formula

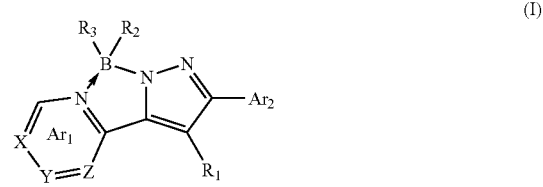

(I)

wherein:

$Ar_1$ represents unsubstituted or substituted monocyclic or polycyclic heteroaryl having a ring nitrogen atom for forming a coordination bond to boron as indicated and optionally one or more additional ring nitrogen atoms subject to the proviso that nitrogen atoms do not occur in adjacent positions, X and Z being carbon or nitrogen and Y being carbon or optionally nitrogen if neither of X and Z is nitrogen, said substituents if present being selected from substituted and unsubstituted hydrocarbyl, substituted and unsubstituted hydrocarbyloxy, fluorocarbon, halo, nitrile, amino alkylamino, dialkylamino or thiophenyl;

$Ar_2$ represents monocyclic or polycyclic aryl or heteroaryl optionally substituted with one or more substituents selected from substituted and unsubstituted hydrocarbyl, substituted and unsubstituted hydrocarbyloxy, fluorocarbon, halo, nitrile, amino, alkylamino, dialkylamino or thiophenyl;

$R_1$ represents hydrogen, substituted or unsubstituted hydrocarbyl, halohydrocarbyl or halo; and $R_2$ and $R_3$ each independently represent alkyl, cycloalkyl, cycloalkylalkyl, haloalkyl, halo or monocyclic or polycyclic aryl, heteroaryl, aralkyl or heteroaralkyl optionally substituted with one or more of alkyl, cycloalkyl, cycloalkylalkyl, haloalkyl, aryl, aralkyl, alkoxy, aryloxy, halo, nitrile, amino, alkylamino or dialkylamino.

$Ar_1$ typically represents monocyclic or bicyclic heteroaryl in which the ring heteroatoms are nitrogen, e.g. pyridyl, pyrimidyl, pyrazinyl, quinolinyl, iso-quinolinyl, quinoxalinyl, or quinazolinyl which may be unsubstituted or may be substituted with one or more cycloalkyl, cycloalkylalkyl, haloalkyl, aryl, aralkyl, alkoxy, aryloxy, halo, nitrile, amino, alkylamino or dialkylamino groups. Preferred are groups selected from alkyl, halocarbon or halo substituents e.g. methyl, methoxy, trifluoromethyl or fluoro.

$Ar_2$ typically represents monocyclic or polycyclic aryl, most usually phenyl or naphthyl, but also fluorenyl and 2-6 polycyclic aryl e.g. anthracenyl, phenanthrenyl, pyrenyl or perylenyl which may be unsubstituted or substituted with e.g. alkyl, cycloalkyl, cycloalkylalkyl, haloalkyl, aryl, aralkyl, alkoxy, aryloxy, halo, nitrile, amino, alkylamino or dialkylamino. Preferred substituents include methyl, methoxy, trifluoromethyl, fluoro and nitrile.

$R_1$ most usually represents hydrogen, but it may also represent alkyl, cycloalkyl, cycloalkylalkyl, haloalkyl, and monocyclic or polycyclic aryl, heteroaryl, aralkyl and heteroaralkyl. Preferred non-hydrogen substituents are methyl, trifluoromethyl and fluoro.

$R_2$ and $R_3$ typically represent phenyl or 4-subsitiuted phenyl wherein the substituent in the 4-position is $C_1$-$C_4$ alkyl e.g. methyl or ethyl, trifluoromethyl, methoxy or fluoro. The groups $R_2$ and $R_3$ may be derived from e.g. dimethylborinic acid, dimethylborinic anhydride, diethylborinic acid, diethylborinic anhydride, dicyclohexylborinic acid, dicyclohexylborinic anhydride, diphenylborinic acid, diphenylborinic anhydride, di-p-tolylborinic acid (see US 2002/0161230, Meudt et al, Clariant Corporation), and bis(pentafluorophenyl)borinic acid and its anhydride.

According to an alternative definition of the invention there is provided a boron complex of formula

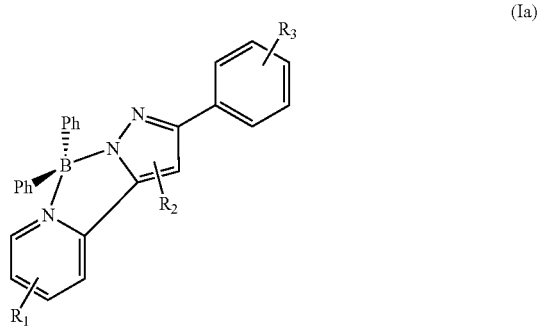

(Ia)

where

Ph is an unsubstituted or substituted phenyl group where the substituents can be the same or different and are selected from hydrogen, and substituted and unsubstituted hydrocarbyl groups such as substituted and unsubstituted aliphatic groups, substituted and unsubstituted aromatic, heterocyclic and polycyclic ring structures, fluorocarbons such as trifluoryl methyl groups, halogens such as fluorine or thiophenyl groups; and R, $R_1$ and $R_2$ can be hydrogen or substituted or unsubstituted hydrocarbyl groups, such as substituted and unsubstituted aromatic, heterocyclic and polycyclic ring structures, fluorine, fluorocarbons such as trifluoryl methyl groups, halogens such as fluorine or thiophenyl groups or nitrile.

Examples of R and/or $R_1$ and/or $R_2$ and/or $R_3$ in Formula (1a) include aliphatic, aromatic and heterocyclic alkoxy, aryloxy and carboxy groups, substituted and substituted phenyl, fluorophenyl, biphenyl, phenanthrene, anthracene, naphthyl and fluorene groups alkyl groups such as t-butyl, heterocyclic groups such as carbazole.

The substituents in the above mentioned compounds are advantageously selected so that the compounds sublime without decomposition in vacuo (e.g. at $10^{-5}$ to $10^{-7}$ Torr) at a temperature of from 120-250° C.

According to a further aspect of the invention, there is also provided a process for manufacturing a compound of the formula (I) as defined above, which comprises condensing a diketone of the formula:

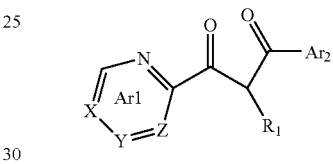

with hydrazine to give a pyrazole of the formula

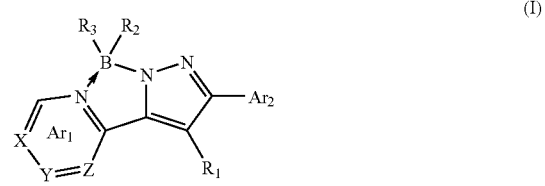

(I)

and esterifying the above pyrazole with a borinic acid of the formula $R_2R_3BOH$ or an anhydride of formula $R_2R_3BOBR_3R_2$ thereof to give the compound of formula (I), atoms X, Y and Z, the rings $Ar_1$, $Ar_2$ and the substituents $R_1$-$R_3$ having the same meanings as for formula (I).

The starting materials for the diketone may be made by standard methods for the production of 1,3-diones e.g. condensation in the presence of a base of an ester of the corresponding unsubstituted or substituted monocyclic or polycyclic heteroarylcarboxylic acid and the corresponding monocyclic or polycyclic aryl- or heteroaryl-ethanone.

The invention also provides an electroluminescent device which comprises a first electrode, a layer of an electroluminescent material and a second electrode in which the electroluminescent material is a complex of formula (I) or (Ia).

The thickness of the layer of the electroluminescent material is preferably from 10-250 nm, more preferably 20-75 nm.

The first electrode can function as the anode and the second electrode can function as the cathode and preferably there is a layer of a hole transporting material between the anode and the layer of the electroluminescent material.

The hole transporting material can be any of the hole transporting materials currently used in electroluminescent devices.

For example, it can be an amine complex such as a-NBP, poly(vinylcarbazole), N,N'-diphenyl-N,N'-bis(3-methylphenyl)-1,1'-biphenyl-4,4'-diamine (TPD), an unsubstituted or substituted polymer of an amino substituted aromatic compound, a polyaniline, substituted polyanilines, polythiophenes, substituted polythiophenes, polysilanes etc. Examples of polyanilines are polymers of

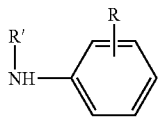 (II)

where R is in the ortho- or meta-position and is hydrogen, C1-18 alkyl, C1-6 alkoxy, amino, chloro, bromo, hydroxy or the group

where R is alky or aryl and R' is hydrogen, C1-6 alkyl or aryl with at least one other monomer of formula I above.

Alternatively the hole transporting material can be a polyaniline. Polyanilines that can be used in the present invention have the general formula

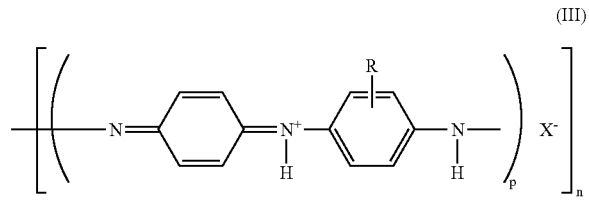 (III)

where p is from 1 to 10 and n is from 1 to 20, R is as defined above and X is an anion, preferably selected from Cl, Br, SO$_4$, BF$_4$, PF$_6$, H$_2$PO$_3$, H$_2$PO$_4$, arylsulphonate, arenedicarboxylate, polystyrenesulphonate, polyacrylate alkysulphonate, vinylsulphonate, vinylbenzene sulphonate, cellulose sulphonate, camphor sulphonates, cellulose sulphate or a perfluorinated polyanion. Examples of arylsulphonates are p-toluenesulphonate, benzenesulphonate, 9,10-anthraquinonesulphonate and anthracenesulphonate. An example of an arenedicarboxylate is phthalate and an example of arenecarboxylate is benzoate.

We have found that protonated polymers of the unsubstituted or substituted polymers of an amino substituted aromatic compound such as a polyaniline are difficult to evaporate or cannot be evaporated. However we have surprisingly found that if the unsubstituted or substituted polymer of an amino substituted aromatic compound is deprotonated then it can be easily evaporated, i.e. the polymer is evaporable. Preferably evaporable deprotonated polymers of unsubstituted or substituted polymers of an amino substituted aromatic compound are used. The de-protonated unsubstituted or substituted polymer of an amino substituted aromatic compound can be formed by deprotonating the polymer by treatment with an alkali such as ammonium hydroxide or an alkali metal hydroxide such as sodium hydroxide or potassium hydroxide. The degree of protonation can be controlled by forming a protonated polyaniline and de-protonating. Methods of preparing polyanilines are described in the article by A. G. MacDiarmid and A. F. Epstein, Faraday Discussions, Chem Soc. 88 P 319 1989. The conductivity of the polyaniline is dependent on the degree of protonation with the maximum conductivity being when the degree of protonation is between 40 and 60% e.g. about 50% for example. Preferably the polymer is substantially fully deprotonated.

A polyaniline can be formed of octamer units i.e. p is four, e.g.

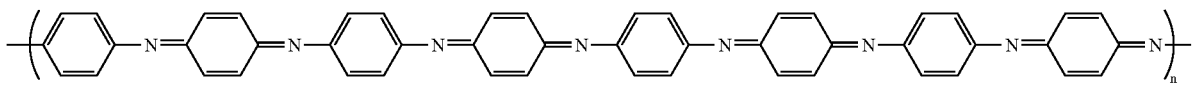

The polyanilines can have conductivities of the order of $1 \times 10^{-1}$ Siemen cm$^{-1}$ or higher. The aromatic rings can be unsubstituted or substituted e.g. by a $C_1$ to $C_{20}$ alkyl group such as ethyl.

The polyaniline can be a copolymer of aniline and preferred copolymers are the copolymers of aniline with o-anisidine, m-sulphanilic acid or o-aminophenol, or o-toluidine with o-aminophenol, o-ethylaniline, o-phenylene diamine or with amino anthracenes, o-toluidine, o-ethylaniline, m-toluidine, m-ethylaniline etc.

Other polymers of an amino substituted aromatic compound which can be used include substituted or unsubstituted polyaminonapthalenes, polyaminoanthracenes, polyaminophenanthrenes, etc. and polymers of any other condensed polyaromatic compound. Polyaminoanthracenes and methods of making them are disclosed in U.S. Pat. No. 6,153,726. The aromatic rings can be unsubstituted or substituted e.g. by a group R as defined above.

Other hole transporting materials are conjugated polymer and the conjugated polymers which can be used can be any of the conjugated polymers disclosed or referred to in U.S. Pat. No. 5,807,627, PCT/WO90/13148 and PCT/WO92/03490. The preferred conjugated polymers are poly(p-phenylenevinylene) (PPV) and copolymers including PPV. Other preferred polymers are poly(2,5 dialkoxyphenylene vinylene) such as poly[(2-methoxy-5-(2-methoxypentyloxy-1,4-phenylene vinylene)], poly(2-methoxypentyloxy)-1,4-phenylenevinylene), poly(2-methoxy-5-(2-dodecyloxy-1,4-phenylenevinylene) and other poly(2,5 dialkoxyphenylenevinylenes) with at least one of the alkoxy groups being a long chain solubilising alkoxy group, poly fluorenes and oligofluorenes, polyphenylenes and oligophenylenes, polyanthracenes and oligo anthracenes, ploythiophenes and oligothiophenes. In PPV the phenylene ring may optionally carry one or more substituents e.g. each independently selected from alkyl, preferably methyl, alkoxy, preferably methoxy or ethoxy.

In poly(fluorene), the fluorene ring may optionally carry one or more substituents e.g. each independently selected from alkyl, preferably methyl, alkoxy, preferably methoxy or ethoxy.

Any poly(arylenevinylene) including substituted derivatives thereof can be used and the phenylene ring in poly(p-phenylenevinylene) may be replaced by a fused ring system such as an anthracene or naphthylene ring and the number of vinylene groups in each polyphenylenevinylene moiety can be increased e.g. up to 7 or higher.

The conjugated polymers can be made by the methods disclosed in U.S. Pat. No. 5,807,627, PCT/WO90/13148 and PCT/WO92/03490.

The thickness of the hole transporting layer is preferably 20 nm to 200 nm.

The polymers of an amino substituted aromatic compound such as polyanilines referred to above can also be used as buffer layers with or in conjunction with other hole transporting materials e.g. between the anode and the hole transporting layer. Other buffer layers can be formed of phthalocyanines such as copper phthalocyanine.

The structural formulae of some other hole transporting materials are shown in FIGS. 3 to 7 of the drawings, where $R_1$, $R_2$ and $R_3$ can be the same or different and are selected from hydrogen, and substituted and unsubstituted hydrocarbyl groups such as substituted and unsubstituted aliphatic groups, substituted and unsubstituted aromatic, heterocyclic and polycyclic ring structures, fluorocarbons such as trifluoryl methyl groups, halogens such as fluorine or thiophenyl groups; $R_1$, $R_2$ and $R_3$ can also form substituted and unsubstituted fused aromatic, heterocyclic and polycyclic ring structures and can be copolymerisable with a monomer e.g. styrene. X is Se, S or O, Y can be hydrogen, substituted or unsubstituted hydrocarbyl groups, such as substituted and unsubstituted aromatic, heterocyclic and polycyclic ring structures, fluorine, fluorocarbons such as trifluoryl methyl groups, halogens such as fluorine or thiophenyl groups or nitrile.

Examples of $R_1$ and/or $R_2$ and/or $R_3$ include aliphatic, aromatic and heterocyclic alkoxy, aryloxy and carboxy groups, substituted and substituted phenyl, fluorophenyl, biphenyl, phenanthrene, anthracene, naphthyl and fluorene groups alkyl groups such as t-butyl, heterocyclic groups such as carbazole.

Optionally there is a layer of an electron injecting material between the cathode and the electroluminescent material layer. The electron injecting material is a material which will transport electrons when an electric current is passed through electron injecting materials including TAZ (formula in FIG. 2) or a metal complex such as a metal quinolate e.g. a zirconium quinolate (Zrq4), zinc quinolate, aluminium quinolate, lithium quinolate, $Mx(DBM)_n$ where Mx is a metal and DBM is dibenzoyl methane and n is the valency of Mx e.g Mx is aluminium or chromium. In place of the DBM moiety there can be a Schiff base.

Figure 2:
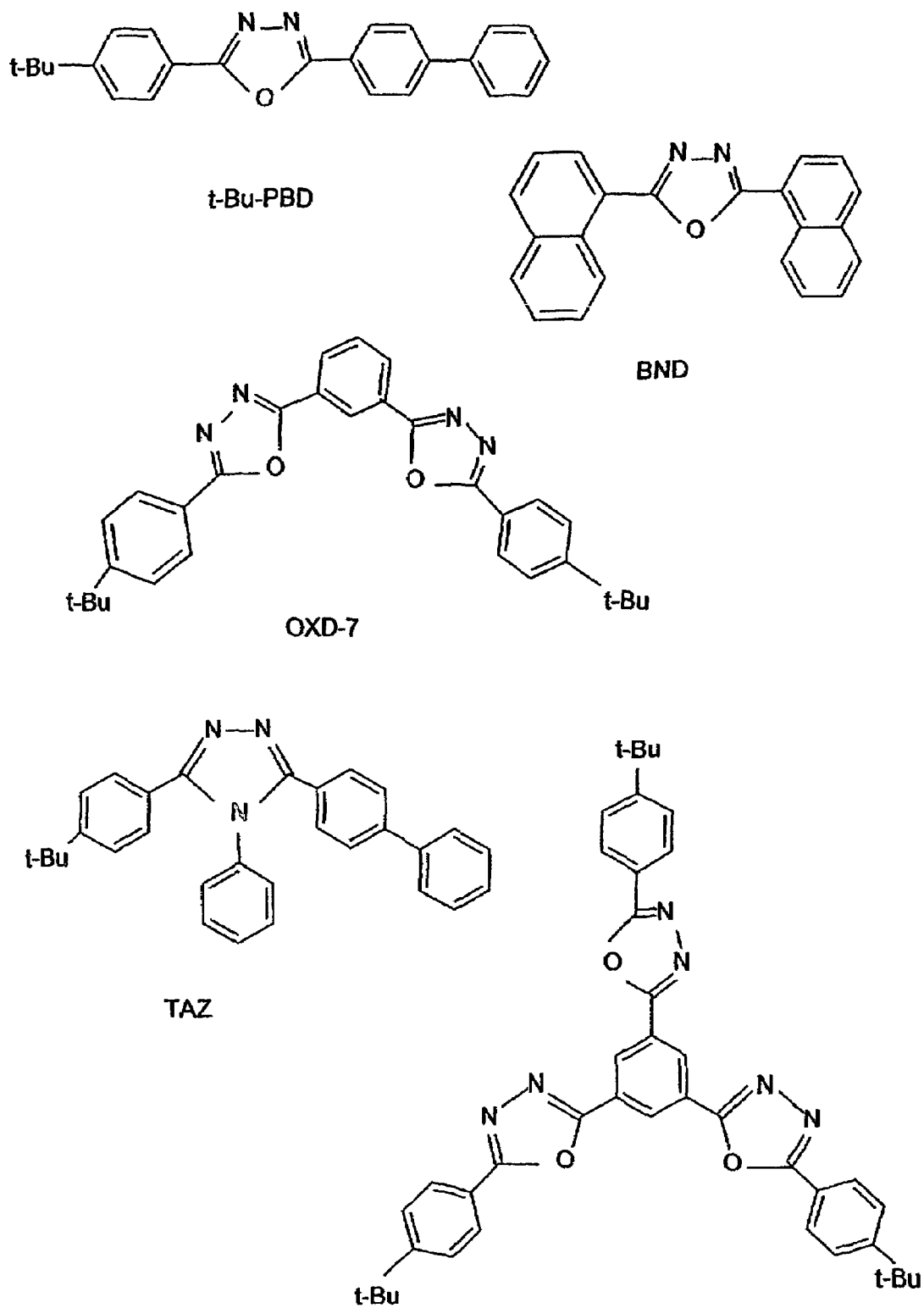
Figure 3:
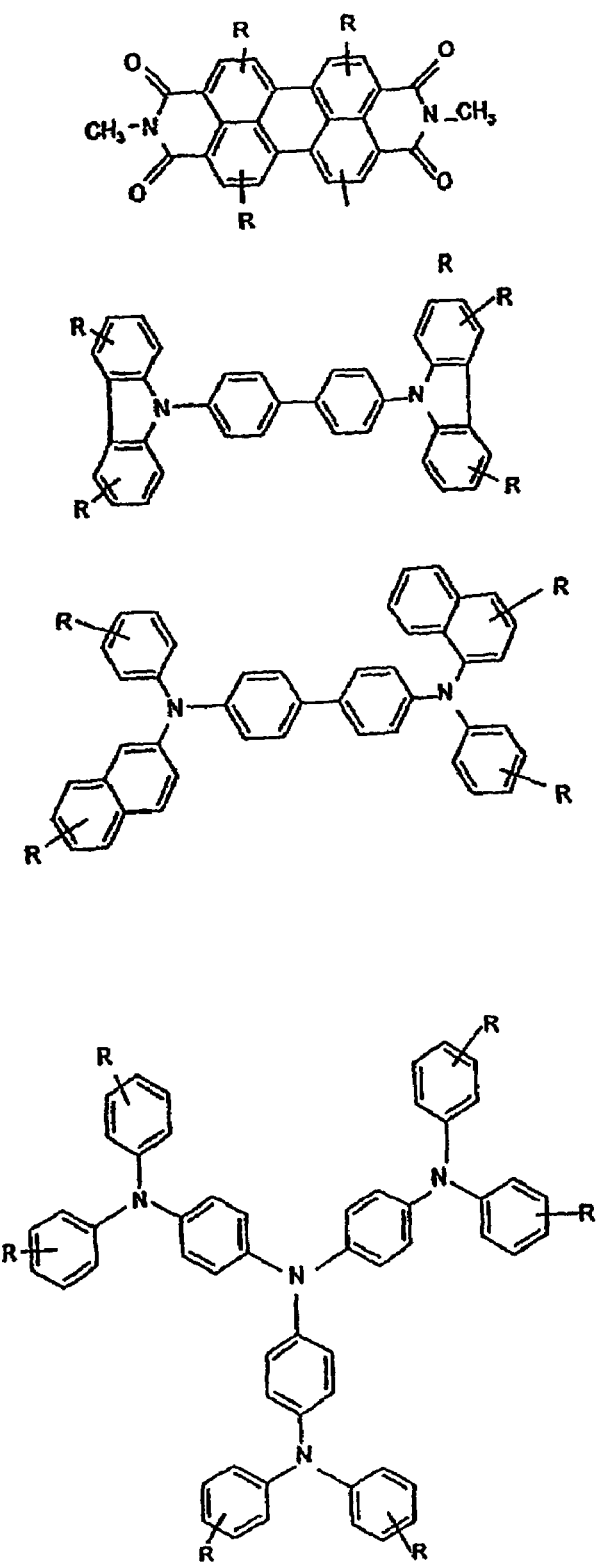
FIGS. 3-7 illustrate chemical formulae for hole transporting materials in accordance with this invention.
Figure 4:
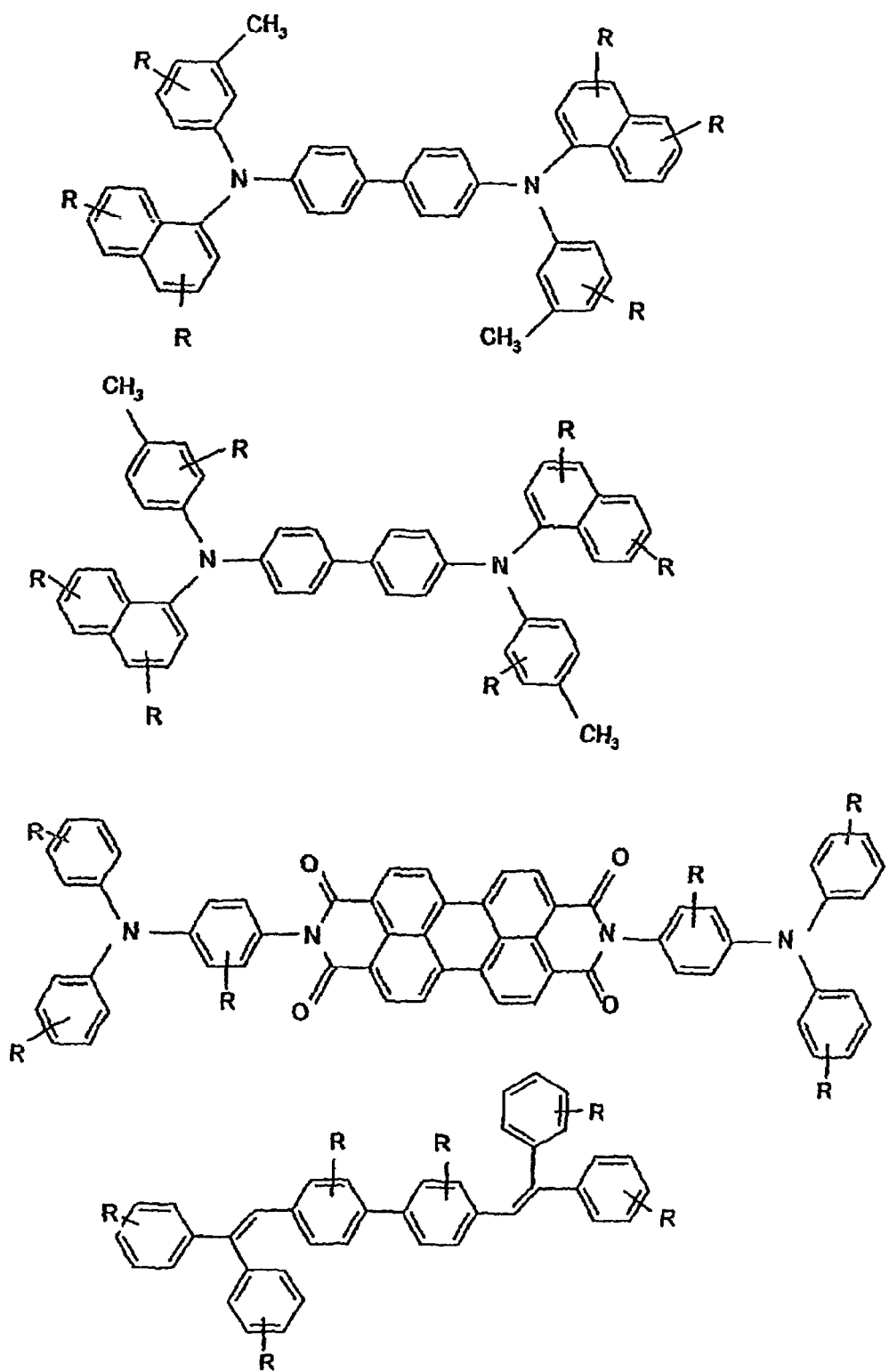
Figure 14A:
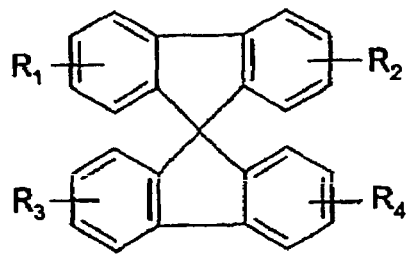
FIGS. 14 and 15 show respectively an electroluminescent spectrum and graphs of luminescence and current density as functions of voltage, and of luminescence and current efficiency as functions of current density for an electroluminescent device according to this invention.
Figure 14B:
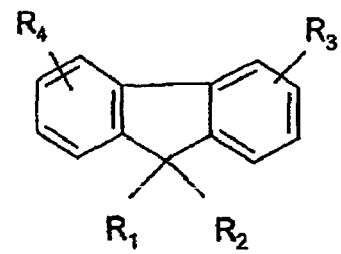
Figure 5:
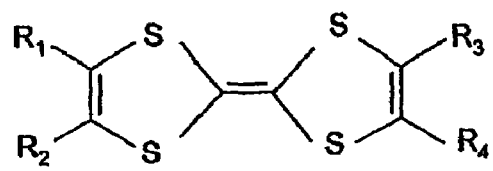
Figure 5:
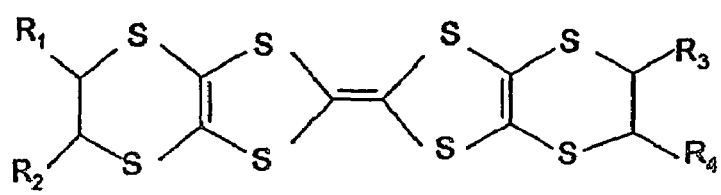
Figure 5:
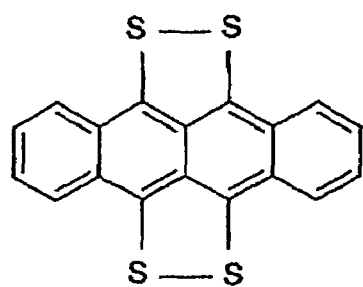
Figure 6:
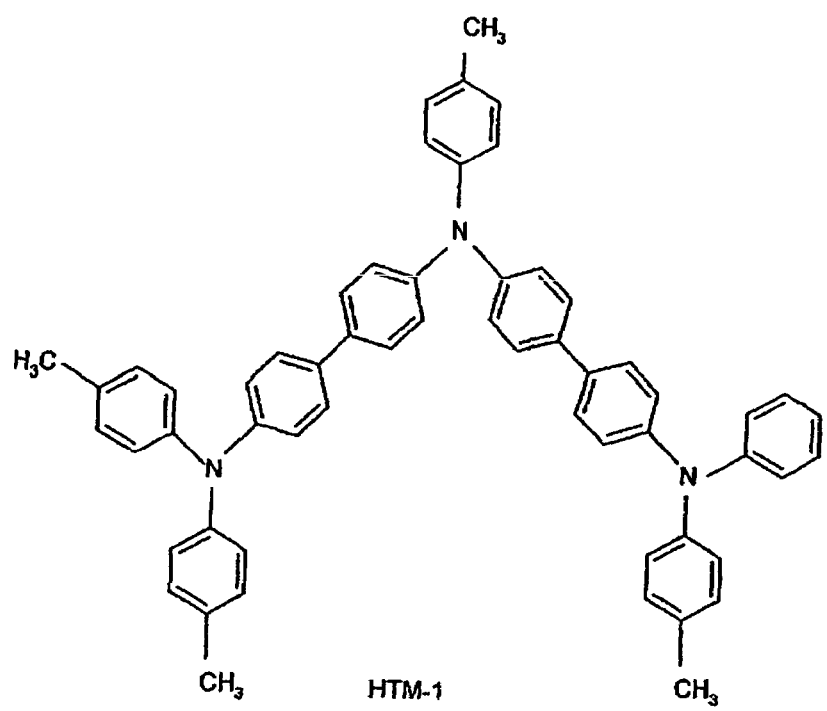
Figure 6:
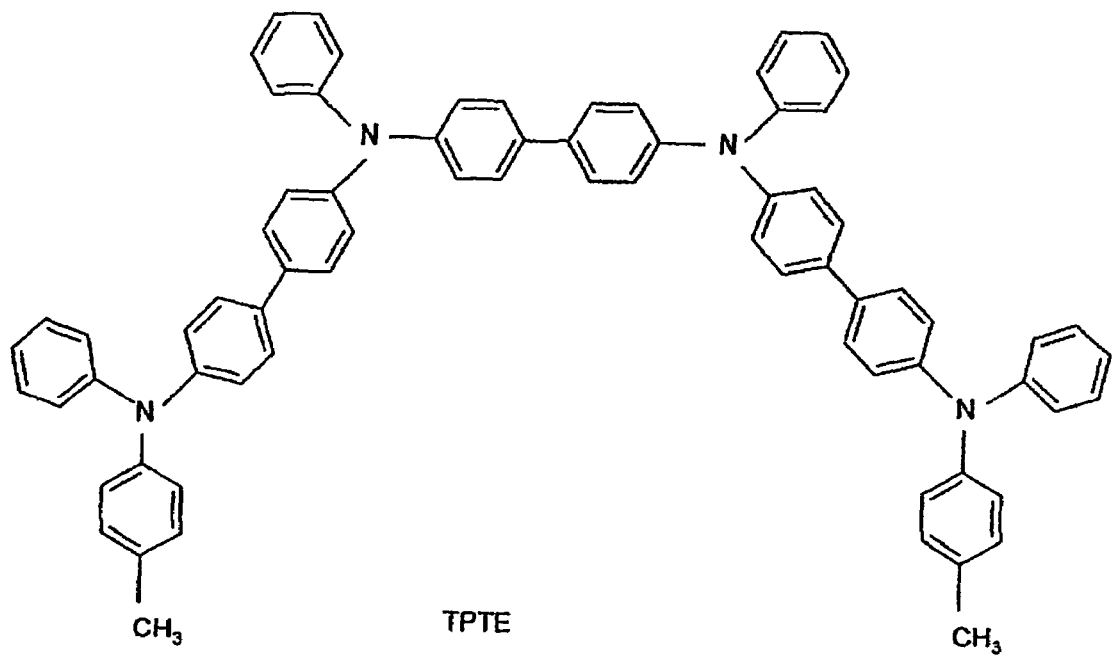

The electron injecting material can also be a cyano anthracene such as 9,10 dicyano anthracene, cyano substituted aromatic compounds, tetracyanoquinidodimethane a polystyrene sulphonate or a compound with the structural formulae shown in FIG. 1 or 2 of the drawings in which the phenyl rings can be substituted with substituents R as defined above. Instead of being a separate layer the electron injecting material can be mixed with the electroluminescent material and co-deposited with it.

Optionally the hole transporting material can be mixed with the electroluminescent material and co-deposited with it and the electron injecting materials and electroluminescent materials can be mixed. The hole transporting materials, the electroluminescent material and the electron injecting materials can be mixed together to form one layer, which simplifies the construction.

The anode is preferably a transparent substrate such as a conductive glass or plastic material which acts as the anode. Preferred substrates are conductive glasses such as indium tin oxide coated glass, but any glass which is conductive or has a conductive layer such as a metal or conductive polymer can be used. Conductive polymers and conductive polymer coated glass or plastics materials can also be used as the substrate. The cathode is preferably a low work function metal e.g. aluminium, barium, rare earth metals, transition metals, calcium, lithium, magnesium and alloys thereof such as silver/magnesium alloys, rare earth metal alloys etc.; aluminium is a preferred metal. A metal fluoride such as an alkali metal e.g. lithium fluoride or rare earth metal fluoride can be used as the second electrode for example by having a metal fluoride layer formed on a metal.

The boron complexes of the present invention include blue emitting electroluminescent materials.

The devices of the present invention can be used as displays in video displays, mobile telephones, portable computers and any other application where a electronically controlled visual image is used. The devices of the present invention can be used in both active and passive applications of such as displays.

In known electroluminescent devices either one or both electrodes can be formed of silicon and the electroluminescent material and intervening layers of a hole transporting and electron transporting materials can be formed as pixels on the silicon substrate. Preferably each pixel comprises at least one layer of an electroluminescent material and a (at least semi-) transparent electrode in contact with the organic layer on a side thereof remote from the substrate.

Preferably, the substrate is of crystalline silicon and the surface of the substrate may be polished or smoothed to produce a flat surface prior to the deposition of electrode, or electroluminescent compound. Alternatively a non-planarised silicon substrate can be coated with a layer of conducting polymer to provide a smooth, flat surface prior to deposition of further materials.

In one embodiment, each pixel comprises a metal electrode in contact with the substrate. Depending on the relative work functions of the metal and transparent electrodes, either may serve as the anode with the other constituting the cathode.

When the silicon substrate is the cathode an indium tin oxide coated glass can act as the anode and light is emitted through the anode. When the silicon substrate acts as the anode, the cathode can be formed of a transparent electrode which has a suitable work function; for example by a indium zinc oxide coated glass in which the indium zinc oxide has a low work function. The anode can have a transparent coating of a metal formed on it to give a suitable work function. These devices are sometimes referred to as top emitting devices or back emitting devices.

The metal electrode may consist of a plurality of metal layers; for example a higher work function metal such as aluminium deposited on the substrate and a lower work function metal such as calcium deposited on the higher work function metal. In another example, a further layer of conducting polymer lies on top of a stable metal such as aluminium.

Preferably, the electrode also acts as a mirror behind each pixel and is either deposited on, or sunk into, the planarised surface of the substrate. However, there may alternatively be a light absorbing black layer adjacent to the substrate.

In still another embodiment, selective regions of a bottom conducting polymer layer are made non-conducting by exposure to a suitable aqueous solution allowing formation of arrays of conducting pixel pads which serve as the bottom contacts of the pixel electrodes.

Blue electroluminescent materials are the most difficult to obtain with satisfactory performance and, in blue monochromatic displays and polychromatic displays, a blue electroluminescent material of the present invention can be used.

As described in WO00/60669 the brightness of light emitted from each pixel is preferably controllable in an analogue manner by adjusting the voltage or current applied by the matrix circuitry or by inputting a digital signal which is converted to an analogue signal in each pixel circuit. The substrate preferably also provides data drivers, data converters and scan drivers for processing information to address the array of pixels so as to create images.

In a further embodiment, each pixel is controlled by a switch comprising a voltage controlled element and a variable resistance element, both of which are conveniently formed by metal-oxide-semiconductor field effect transistors (MOSFETs) or by an active matrix transistor.

The invention is illustrated in the following examples

EXAMPLE 1

Preparation of 2-(2-diphenylboranyl-5-phenylpyrazol-3-yl)pyridine

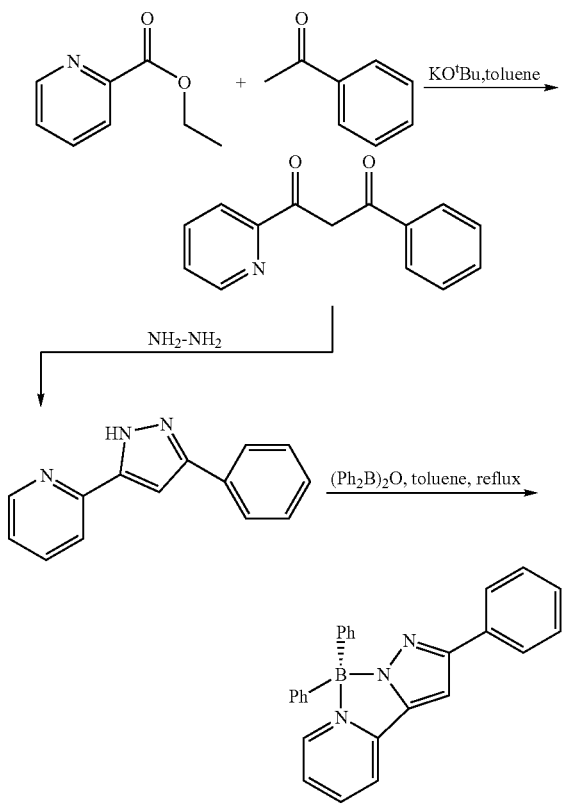

Acetophenone (11.6 mL, 99 mmol), was added to a suspension of potassium tert-butoxide (12.34 g 110 mmol) in toluene (150 mL) and stirred under argon. The flask was then charged with ethyl picolinate (13.4 mL, 99 mmol) and the mixture stirred overnight. The toluene was removed by rotary evaporation and 200 mL of both diethylether and deionised water added. With stirring the mixture was acidified with dilute HCl until the ether layer was dark orange~pH 7). The ether layer was separated, washed with deionised water (3×100 mL), dried over magnesium sulfate and filtered. The solvent was removed and the solid recrystallised from hot ethanol to yield 1-phenyl-3-pyridin-2-ylpropane-1,3-dione (1) as a pale yellow crystalline solid (15.3 g, 69%).

A 250 mL flask was charged with compound (1) (10 g 44 mmol), a magnetic follower and 150 mL of ethanol. Hydrazine monohydrate (2.15 mL, 44 mmol) was added and the mixture refluxed overnight. On cooling the ethanol was removed and the residue recrystallised from methanol to yield 2-(5-phenylpyrazol-3-yl)pyridine (2) as a pale yellow crystalline solid (9.5 g, 97%).

Figure 8:
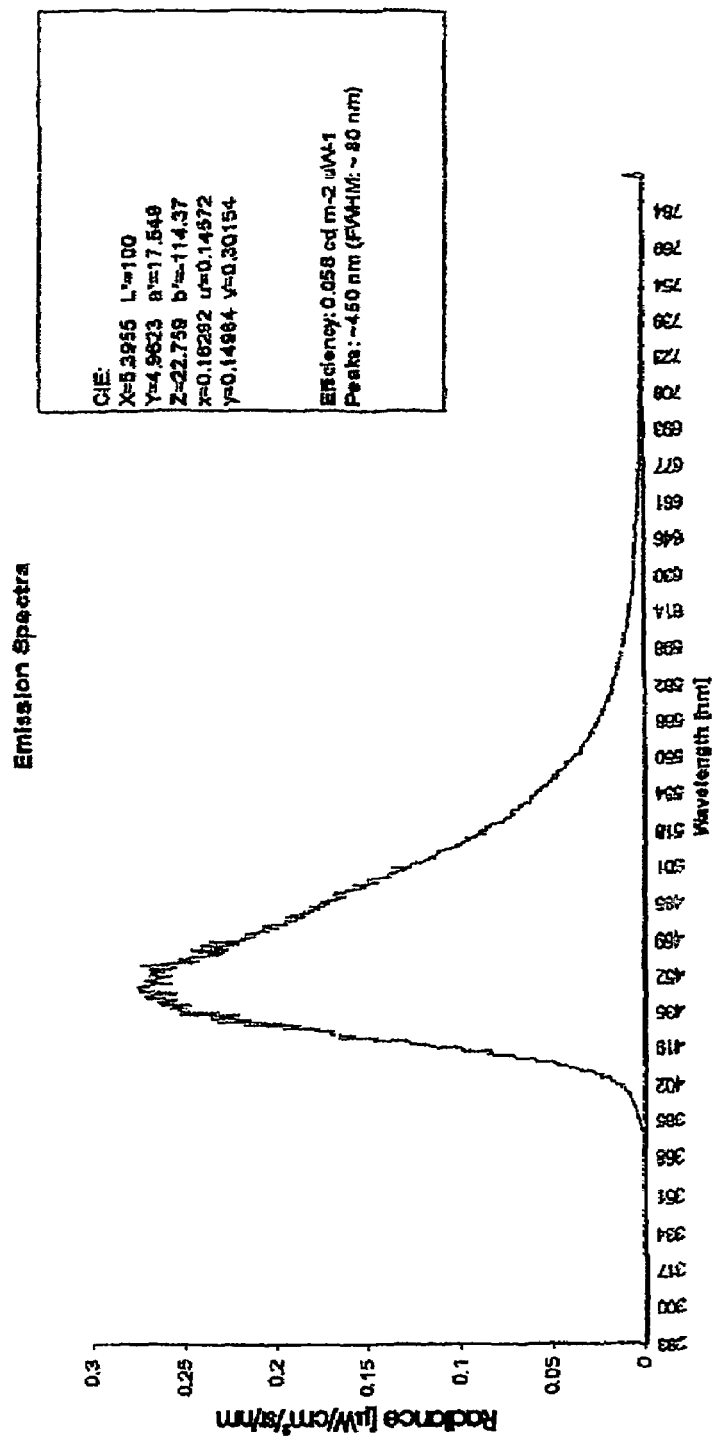
FIGS. 8 and 9 show respectively an emission spectrum and UV absorbance for an electroluminescent complex according to this invention.
Figure 9:
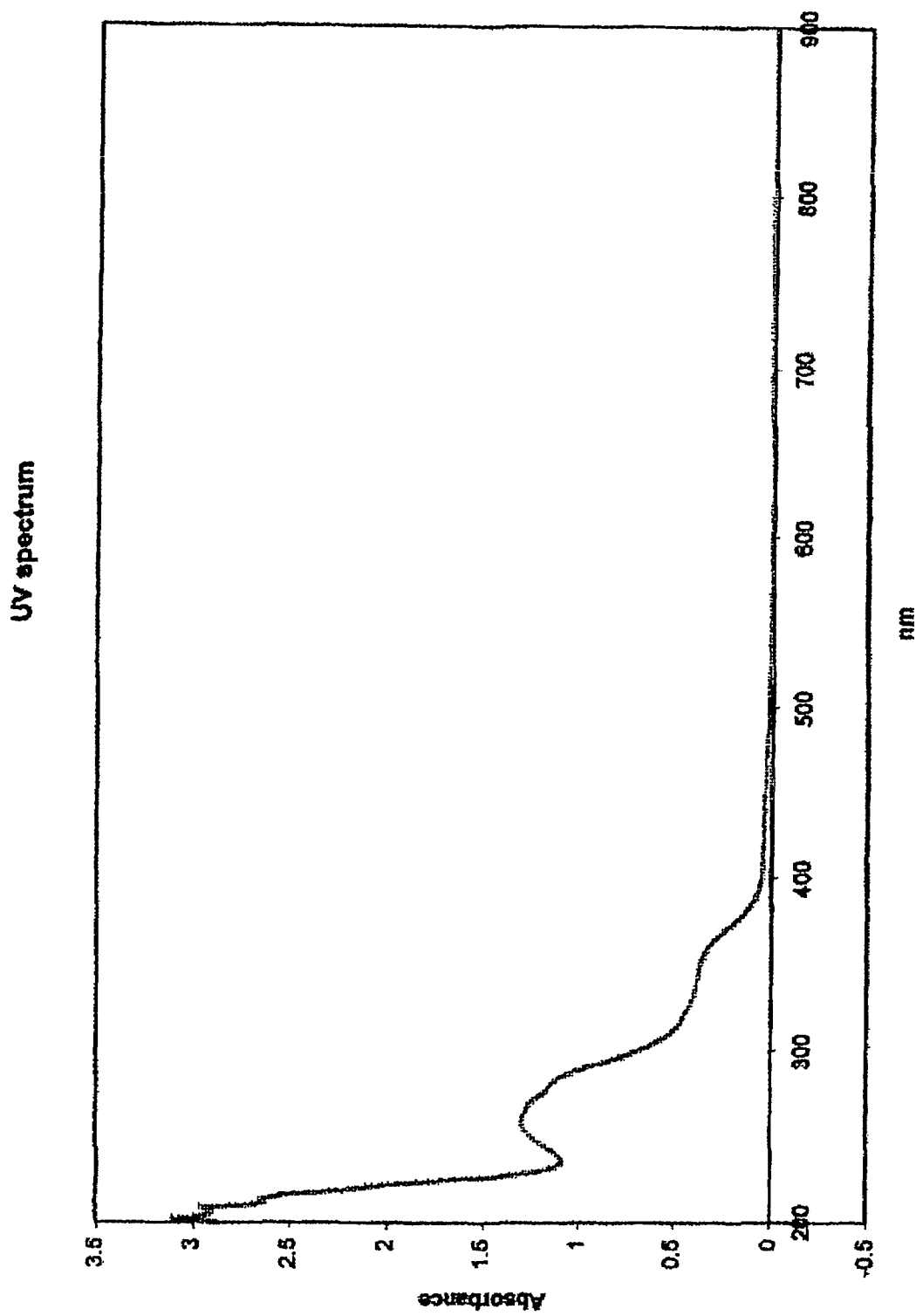

A 150 mL flask was charged with diphenylborinic anhydride (1.00 g, 2.9 mmol), compound (2) (1.28 g, 5.8 mmol) and 100 mL of toluene. The mixture was refluxed until all traces of the anhydride had dissolved and then refluxed for a further 2 hours. On cooling, white crystals were formed. These were collected by filtration and dried under vacuum to give 2.15 g (96%) of 2-(2-diphenylboranyl-5-phenypyrazol-3-yl)pyridine. DSC: Mpt. 261.4-265.2° C. (Recryst. 173.3° C.). The properties of this complex are shown in table 1 below and its emission spectrum and UV absorbance are shown in FIGS. 8 and 9.

EXAMPLE 2

Preparation of 2-(2-diphenylboranyl-5-(4-fluorophenyl)pyrazol-3-yl)pyridine

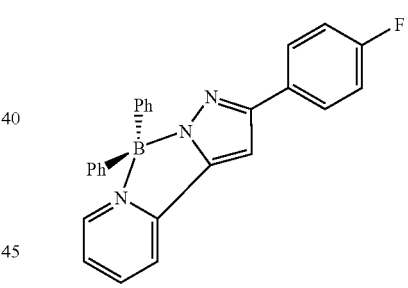

Figure 10:
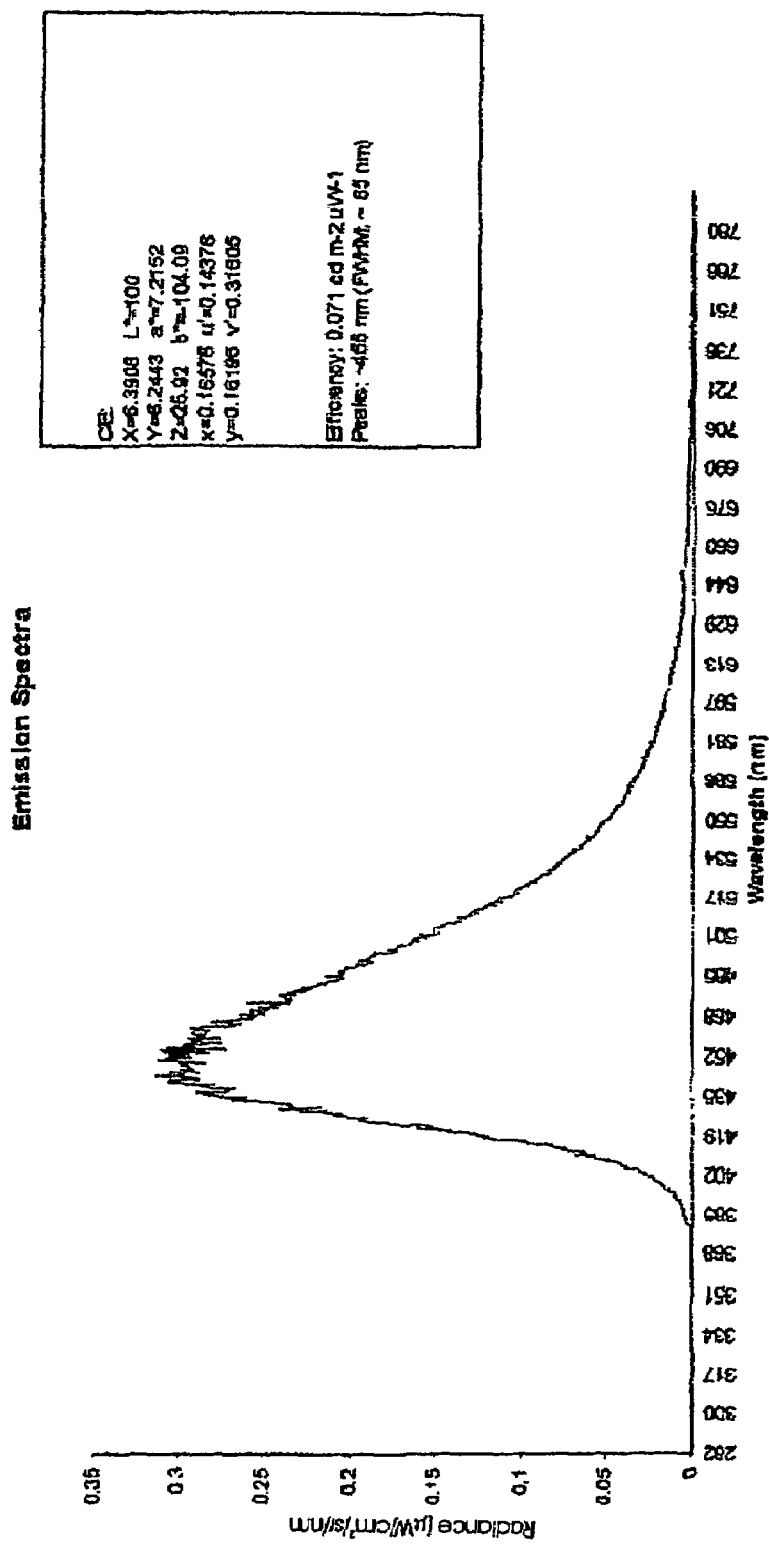
FIGS. 10 and 11 show respectively an emission spectrum and UV absorbance for another electroluminescent complex according to this invention.
Figure 11:
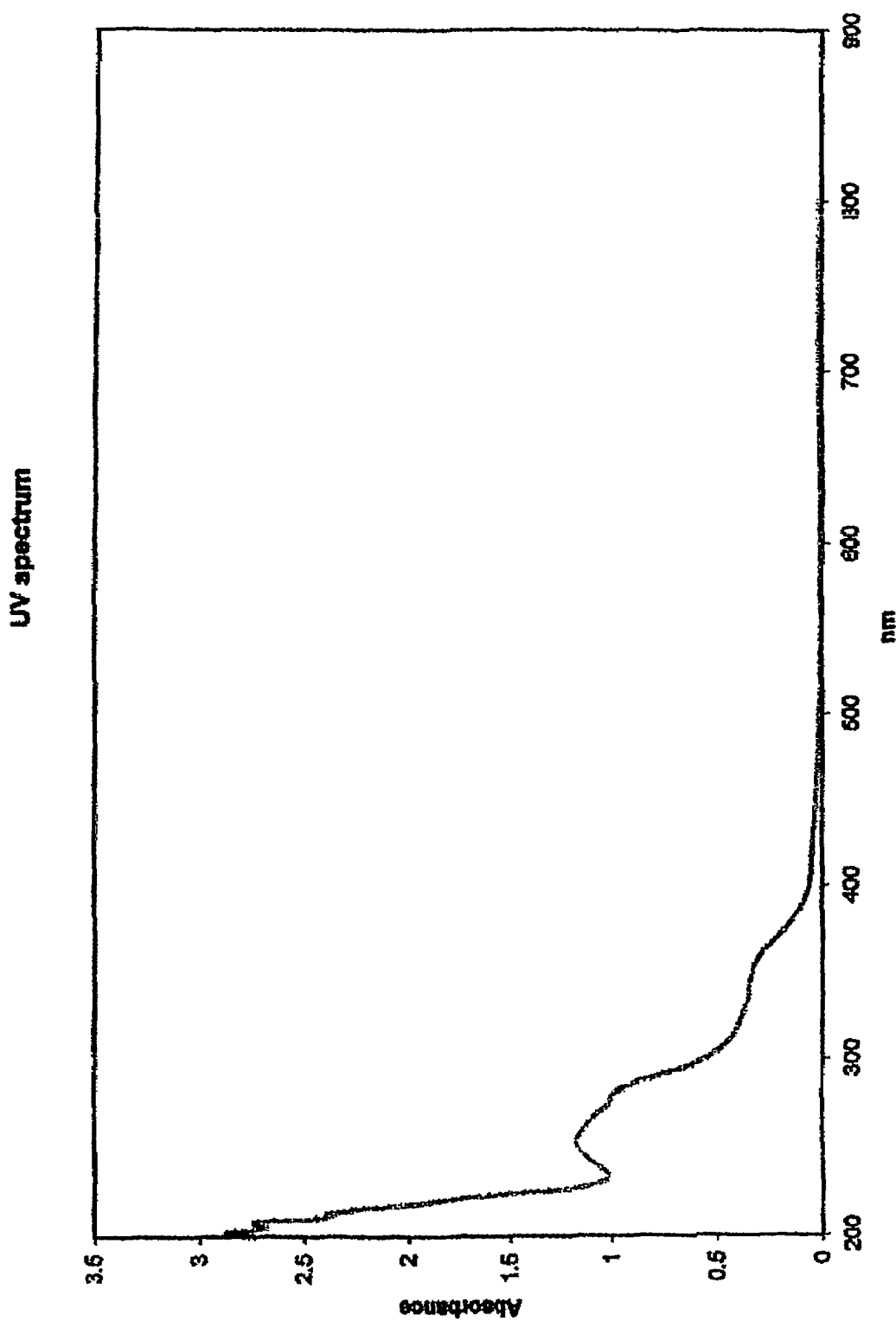

2-(2-diphenylboranyl-5-(4-fluorophenyl)pyrazol-3-yl)pyridine was prepared by the method of example 1 with acetophenone being replaced by 4'-fluoroacetophenone. The diketone was prepared in ~70% yield and the free ligand and boron compounds were formed in 90+% yields. DSC: Mpt. 263.7-266.6° C. (Recryst.196.4° C.). The properties of this complex are shown in table 1 below and its emission spectrum and UV absorbance are shown in FIGS. 10 and 11.

TABLE 1

| Compound of Example | PL Efficiency $Cdm^{-2}\mu w^{-1}$ | Peak Wavelength nm | CIE Coord. x; y | M.P.° C. |
|---|---|---|---|---|
| 1 | 0.071 | ~455 | 0.17; 0.16 | 263-267 |
| 2 | 0.058 | ~450 | 0.16; 0.15 | 261-265 |

The CIE coordinates refer to the CIE xy chromaticity diagram.

EXAMPLES 3-12

The compounds indicated in Table II were prepared as in Example 1, and their properties were as shown in the Table, in which the x and y values in the final two columns are color coordinates.

EXAMPLE 13

A pre-etched ITO (indium tin oxide) coated glass piece (10×10 cm$^2$) was used. A device was fabricated by sequentially forming layers on the ITO by vacuum evaporation, using a Solciet Machine, ULVAC Ltd. Chigacki, Japan; the

TABLE II

Compounds of Examples 3-12

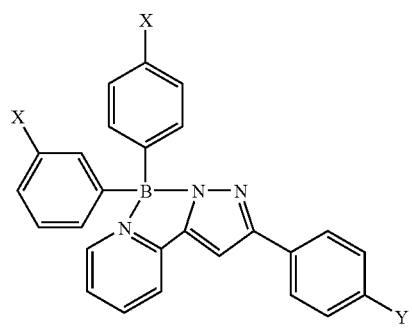

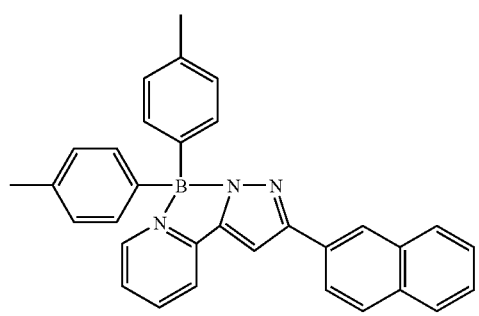

Compound E

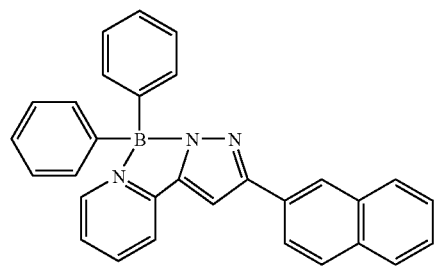

Compound G

| Identity (Ex.) | X | Y | DSC m.p. (° C.) | DSC Tg (° C.) | PL (Film) Peak (nm) | PL (Film) Efficiency (cdm$^{-2}$μW$^{-1}$) | PL (Film) x | PL (Film) y |
|---|---|---|---|---|---|---|---|---|
| A(3) | H | H | 259.1-263.1 | Not observed | 460 | 0.111 | 0.1593 | 0.1968 |
| C(4) | H | CN | 328.2-334.4 | Not observed | 460 | 0.043 | 0.1543 | 0.1257 |
| D(5) | Me | H | 251.8-256 | 95.2 | 460 | 0.036 | 0.1626 | 0.1822 |
| E(6) | FIG. E | | 287-291 | 116 | 475 | 0.09 | 0.1714 | 0.2578 |
| F(7) | H | F | 383-393 | Not observed | 461 | 0.112 | 0.1619 | 0.2015 |
| G(8) | FIG. G | | 313.6-317.5 | 106.8 | 470 | 0.09 | 0.1706 | 0.2572 |
| H(9) | H | Me | 267.5-271.9 | 97.6 | 465 | 0.06 | 0.1668 | 0.2261 |
| I(10) | OMe | Me | 295-300 | 95 | 468 | 0.087 | 0.1740 | 0.2489 |
| K(11) | Me | F | 244-248 | 100 | 460 | 0.06 | 0.1679 | 0.1858 |
| L(12) | Me | CN | 322.6-327.6 | 116.9 | 440 | 0.03 | 0.1625 | 0.1822 | active area of each pixel was 3 mm by 3 mm. The layers comprised:

ITO (H)/CuPc (25 nm)/α-NPB (110 nm)/Compound
      A (35 nm)/Al in which compound A has the formula

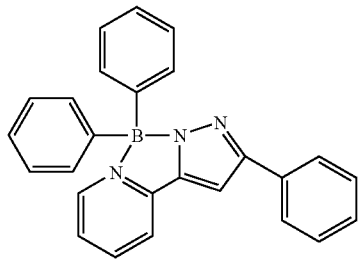

Compound A

Figure 7:
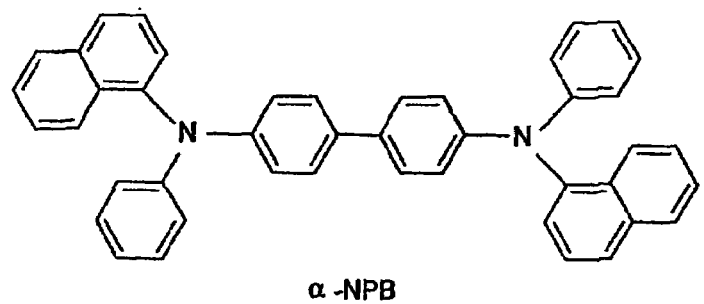
Figure 7:
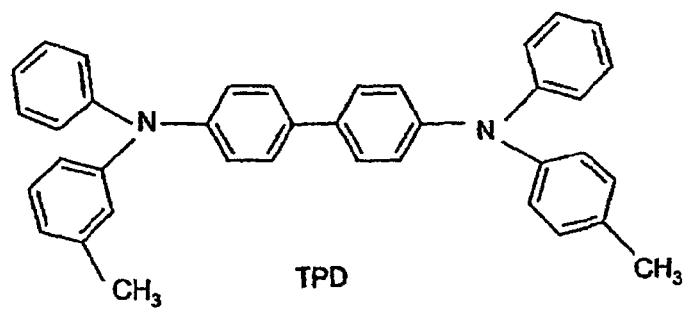
Figure 7:
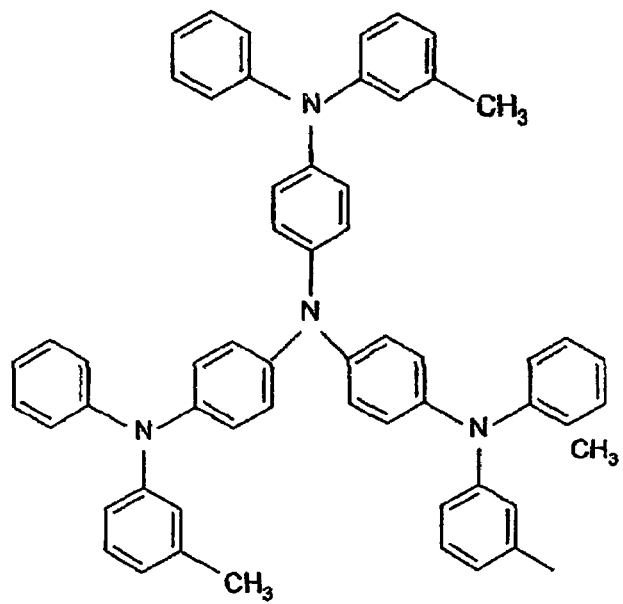

CuPc is a copper phthalocyanine buffer layer and α-NPB is as in FIG. 7. The coated electrode was stored in a vacuum desiccator over a molecular sieve and phosphorous pentoxide until it was loaded into a vacuum coater ($10^{-6}$ torr) and the aluminium top contact was made. The device was then kept in a vacuum desiccator until the electroluminescence studies were performed.

Figure 12:
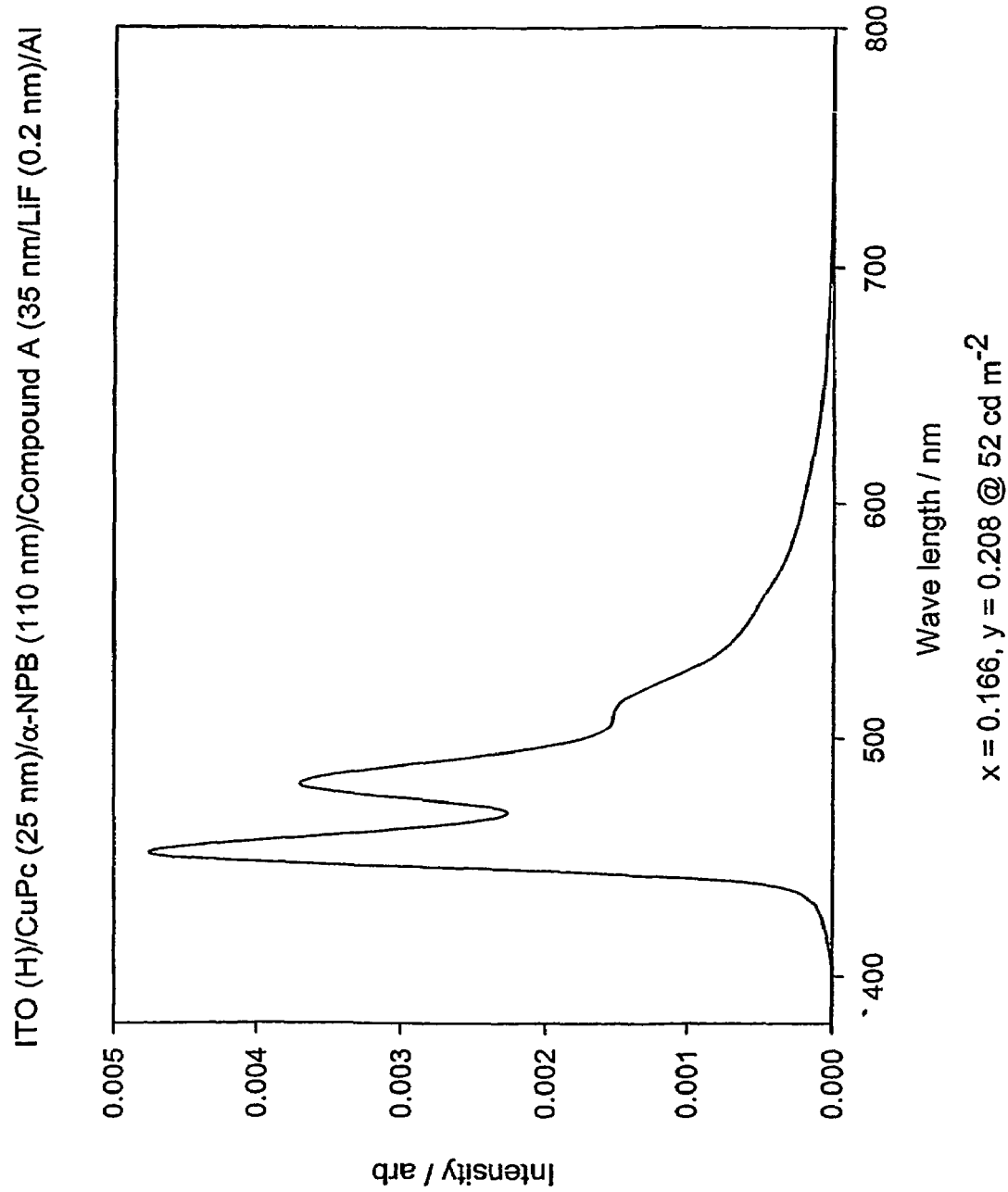
FIGS. 12 and 13 show respectively an electroluminescent spectrum and graphs of luminescence and current density as functions of voltage, and of luminescence and current efficiency as functions of current density for an electroluminescent device according to this invention.
Figure 13:
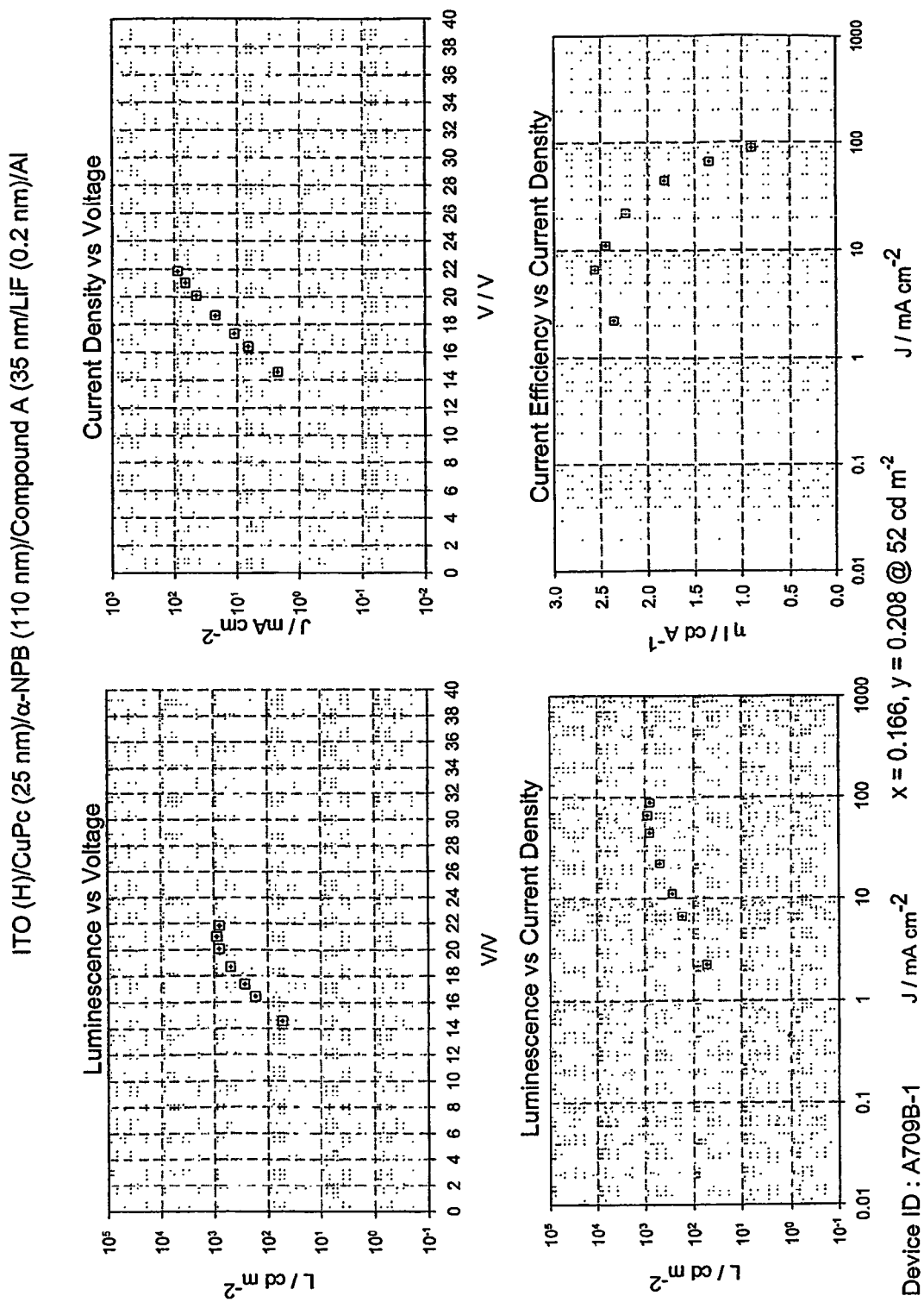

In these studies, the ITO electrode was always connected to the positive terminal. The current vs. voltage studies were carried out on a computer controlled Keithly 2400 source meter. The electroluminescent spectrum was measured and the results shown in FIG. 12. Luminescence and current density were measured as a function of voltage and luminescence and current efficiency were measured as a function of current density with the results shown in FIG. 13.

A further electroluminescent device was made with a cell comprising the following layers, LiF representing lithium fluoride:

ITO (H)/CuPc (25 nm)/α-NPB (85 nm)/Compound A
      (55 nm)/LiF (0.2 nm)/Al .

Figure 14:
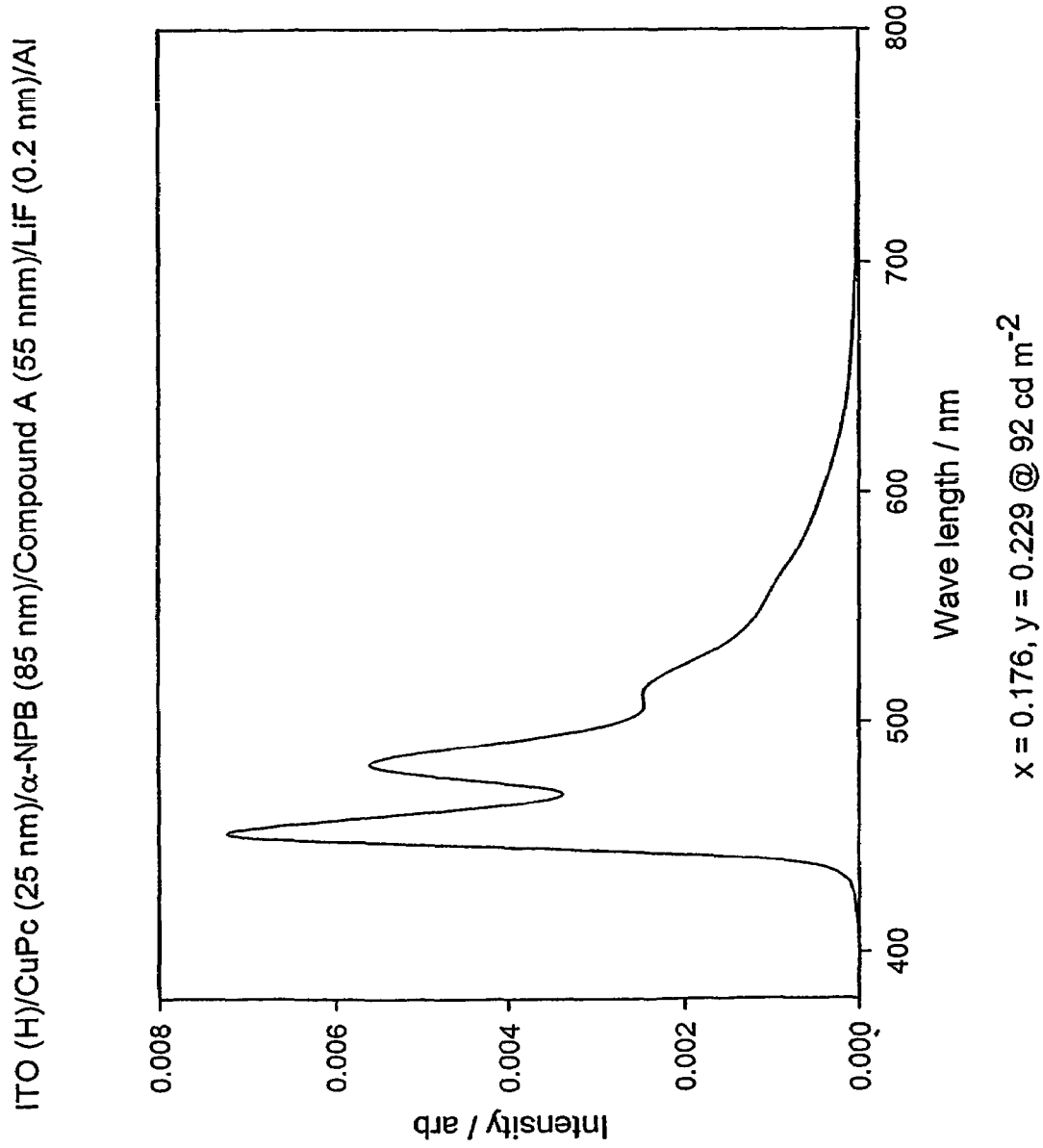
Figure 15:
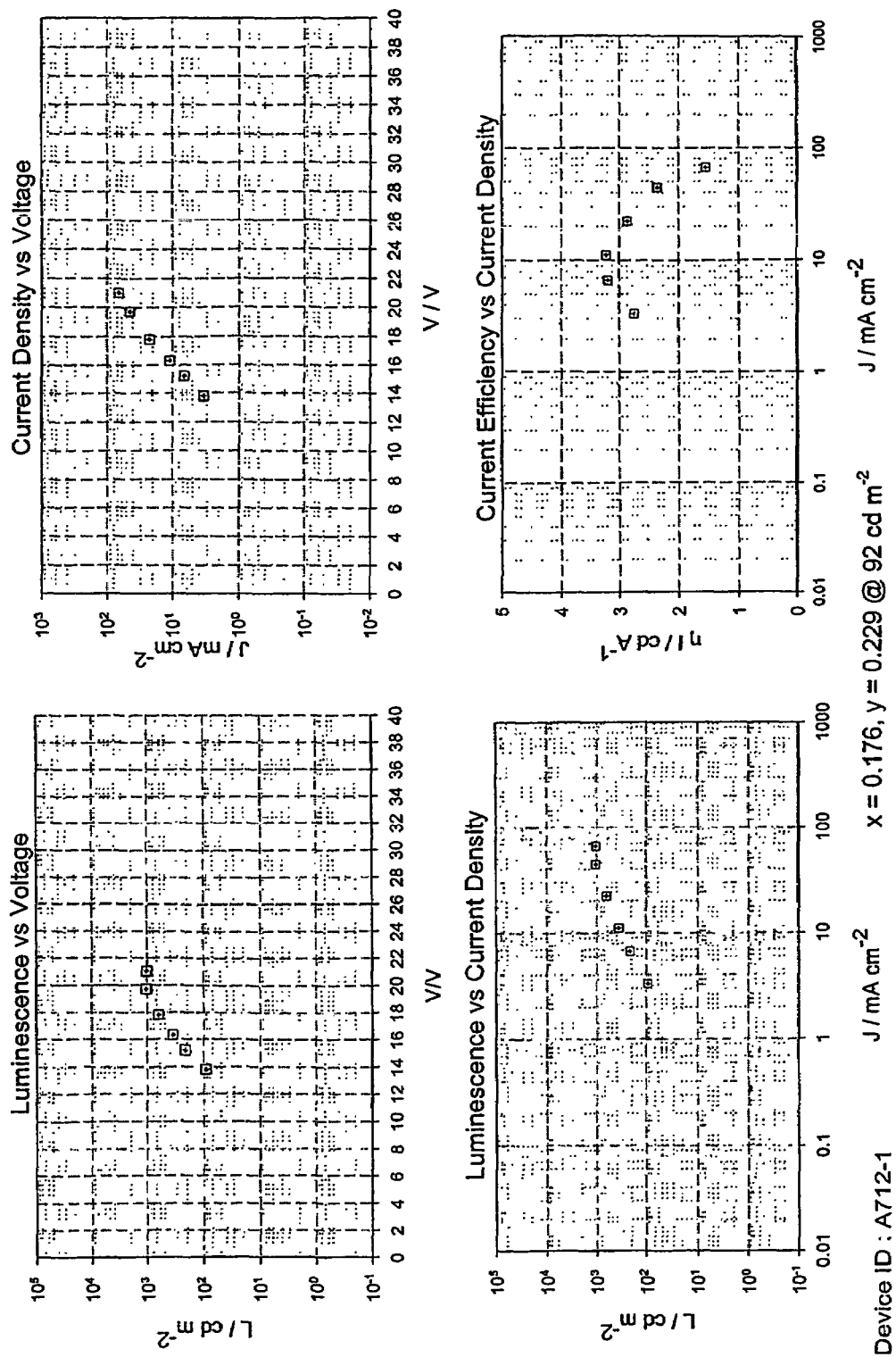
Figure 16:
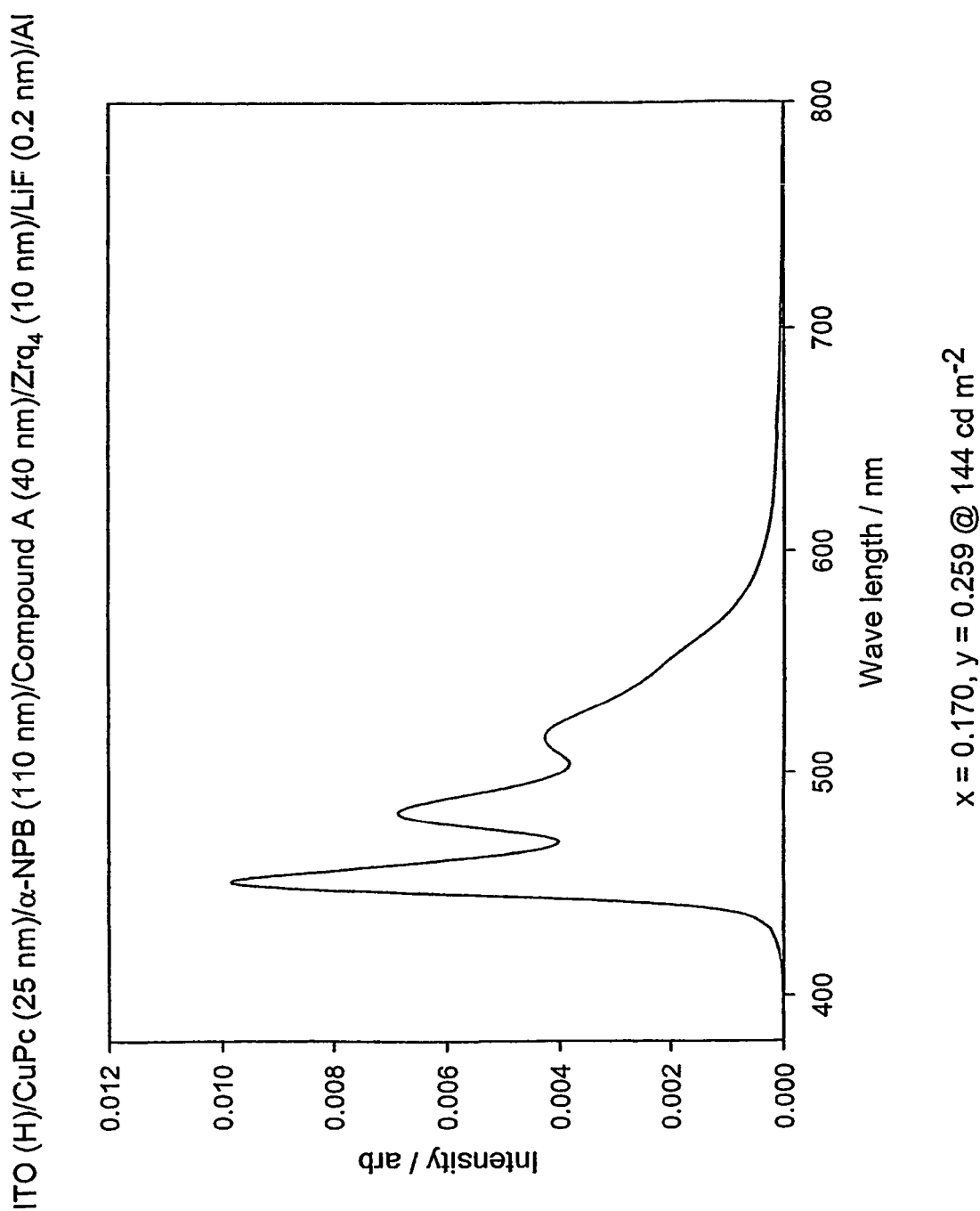
FIGS. 16 and 17 show respectively an electroluminescent spectrum and graphs of luminescence and current density as functions of voltage, and of luminescence and current efficiency as functions of current density for an electroluminescent device according to this invention.
Figure 17:
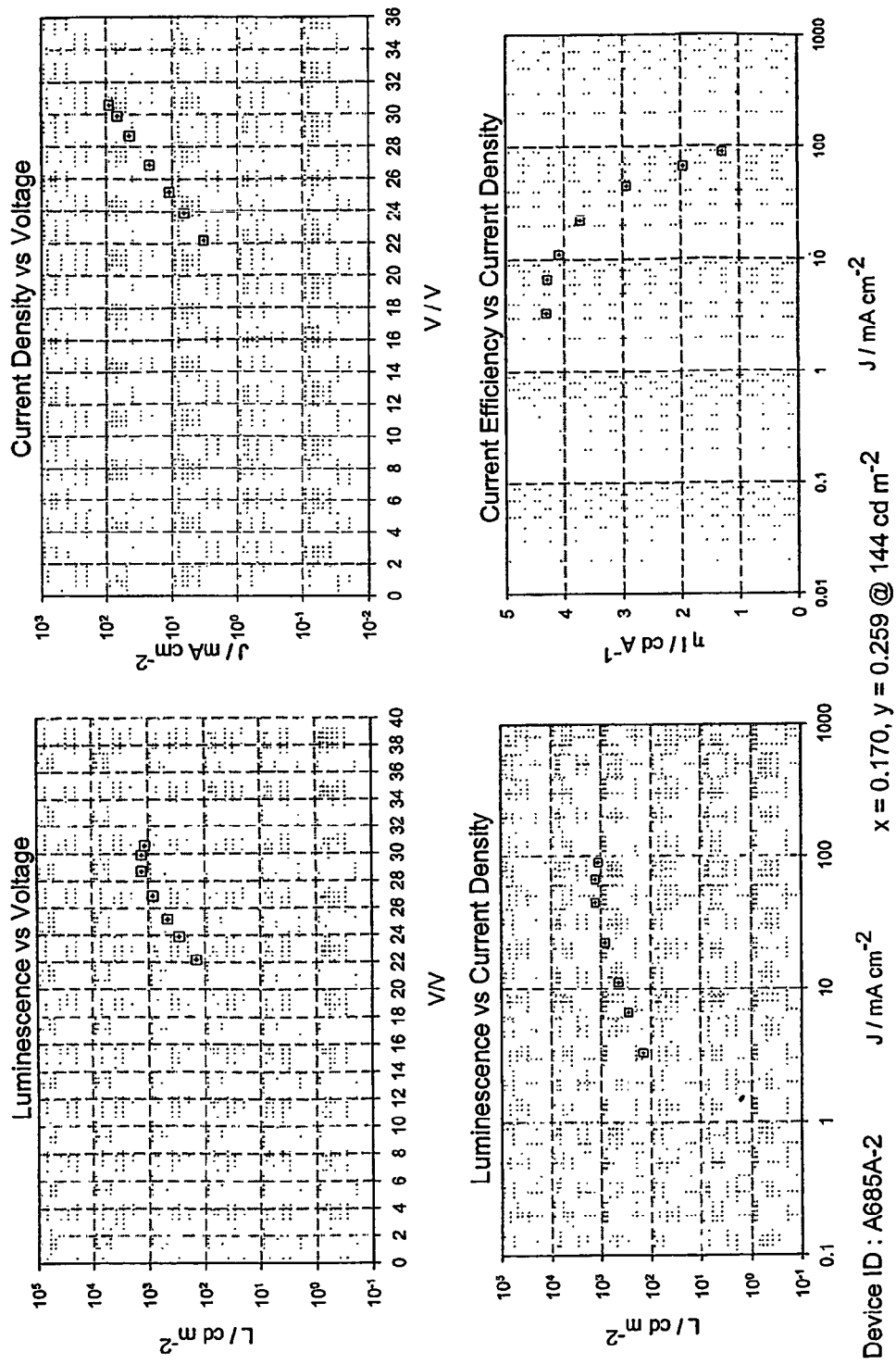

The electroluminescent spectrum was measured and the results shown in FIG. 14. Luminescence and current density were measured as a function of voltage and luminescence and current efficiency were measured as a function of current density with the results shown in FIG. 15. A third electroluminescent device was made with a cell comprising the following layers:

ITO(H)/CuPc (25 nm)/α-NPB (110 nm)/Compound A
      (40 nm)/Zrq$_4$ (10 nm)/LiF (0.2 nm)/Al in which ZrQ$_4$ is zirconium quinolate. The electroluminescent spectrum was measured and the results are shown in FIG. 16. Luminescence and current density were measured as a function of voltage and luminescence and current efficiency were measured as a function of current density with the results shown in FIG. 17. A fourth electroluminescent cell was made comprising the following layers:

ITO(H)/CuPc (25 nm)/α-NPB (110 nm)/Compound B
      (1 mn)/Compound A (40 nm)/Zrq$_4$ (10 nm)/LiF
      (0.2 nm)/Al in which compound B is of formula:

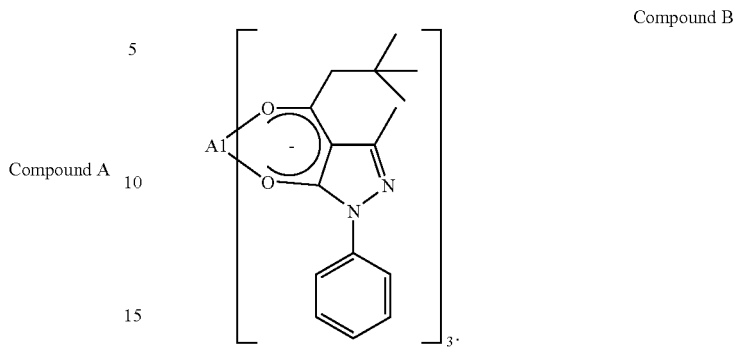

Compound B

Figure 18:
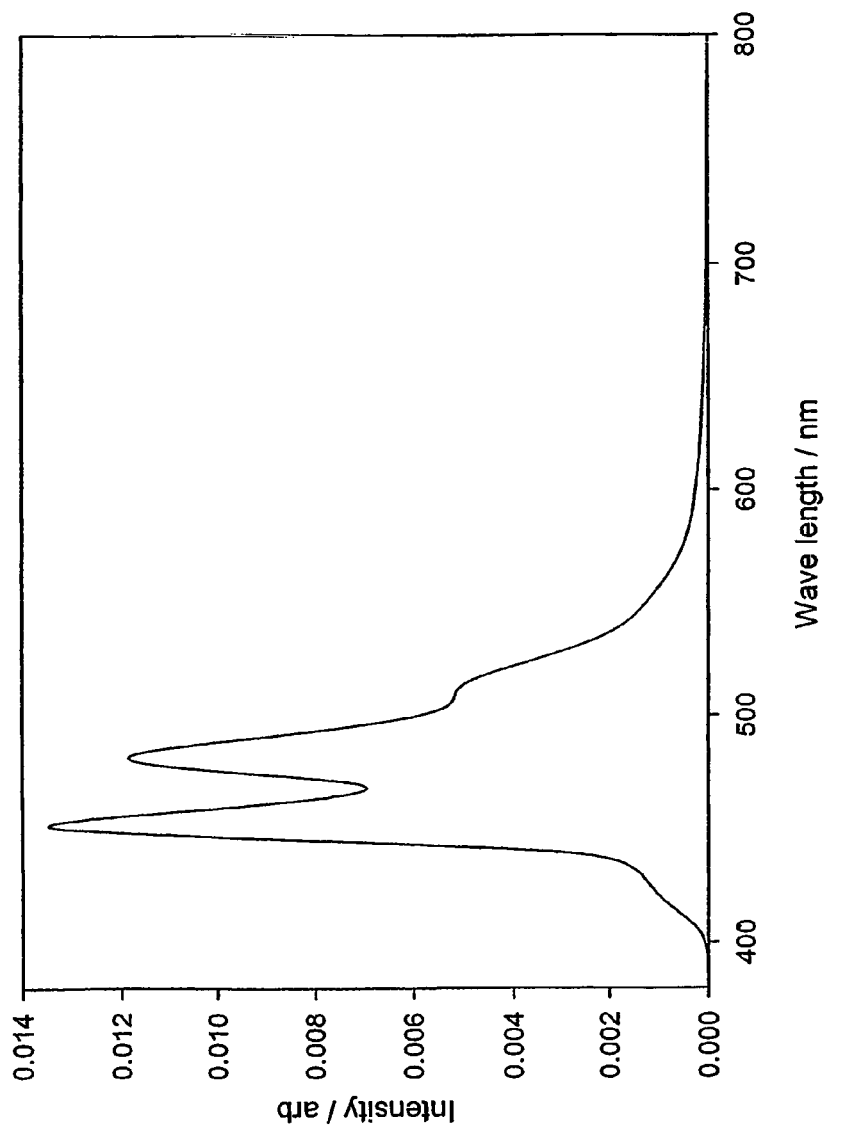
FIGS. 18 and 19 show respectively an electroluminescent spectrum and graphs of luminescence and current density as functions of voltage, and of luminescence and current efficiency as functions of current density for an electroluminescent device according to this invention.
Figure 19:
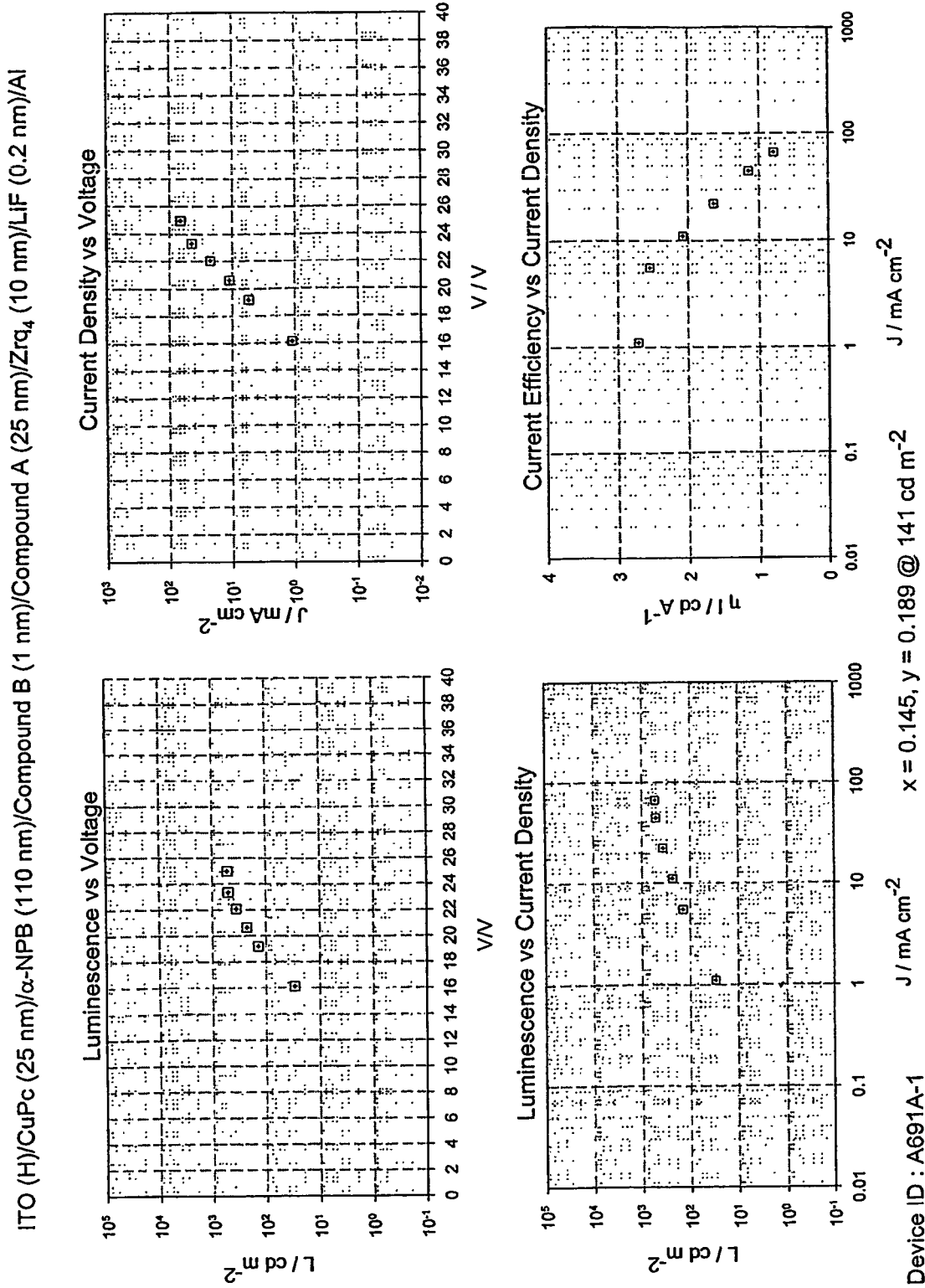

The electroluminescent spectrum was measured and the results are shown in FIG. 18. Luminescence and current density were measured as a function of voltage and luminescence and current efficiency were measured as a function of current density with the results shown in FIG. 19.

EXAMPLE 14

An electroluminescent device was made with the following layers:

ITO(H)/CuPc (25 nm)/α-NPB (110 nm)/Compound C
      (40 nm)/Zrq$_4$ (10 nm)/LiF (0.5 nm)/Al in which compound C is of formula:

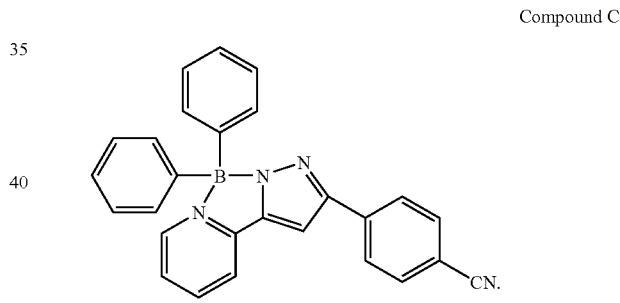

Compound C

Figure 20:
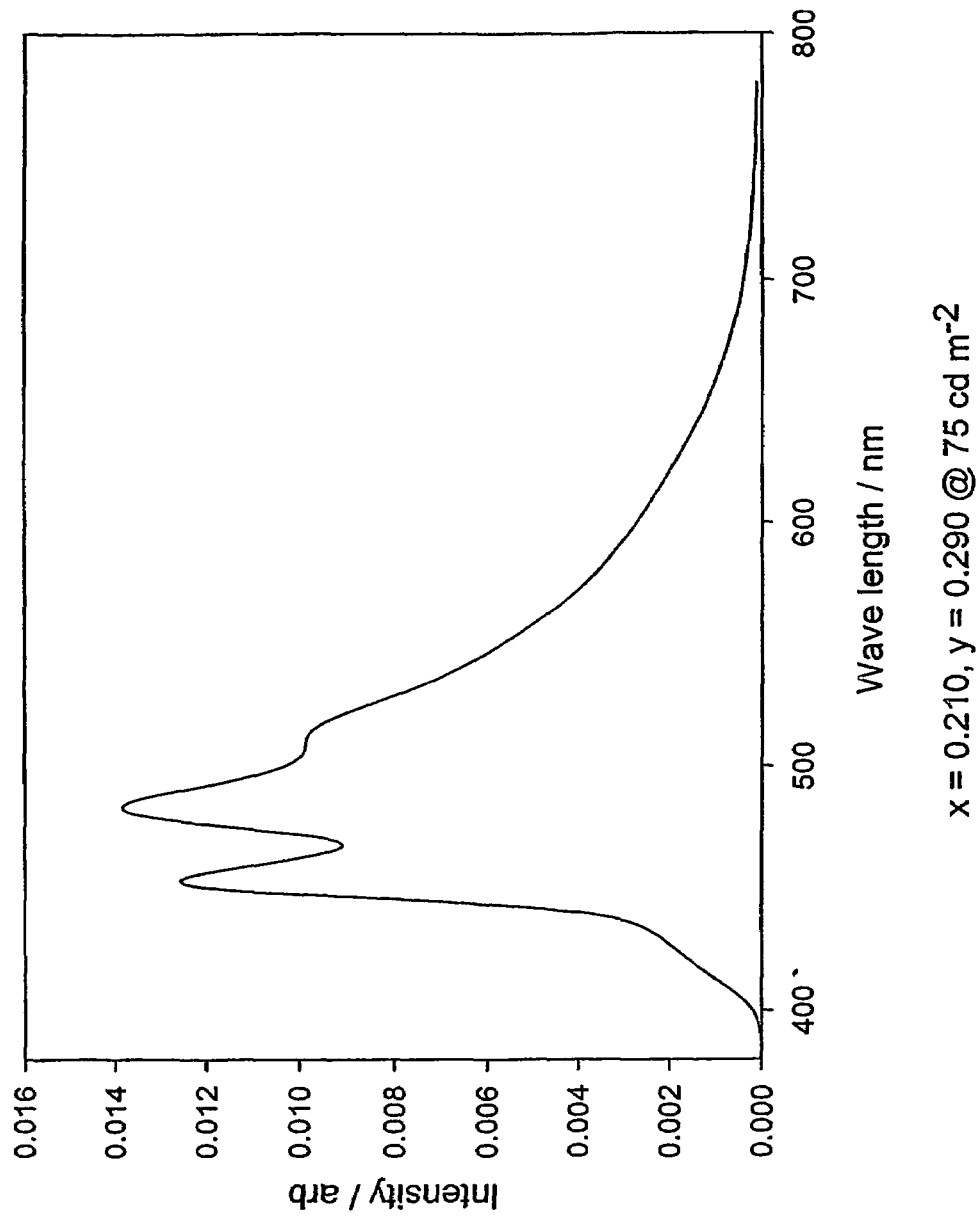
FIGS. 20 and 21 show respectively an electroluminescent spectrum and graphs of luminescence and current density as functions of voltage, and of luminescence and current efficiency as functions of current density for an electroluminescent device according to this invention.
Figure 21:
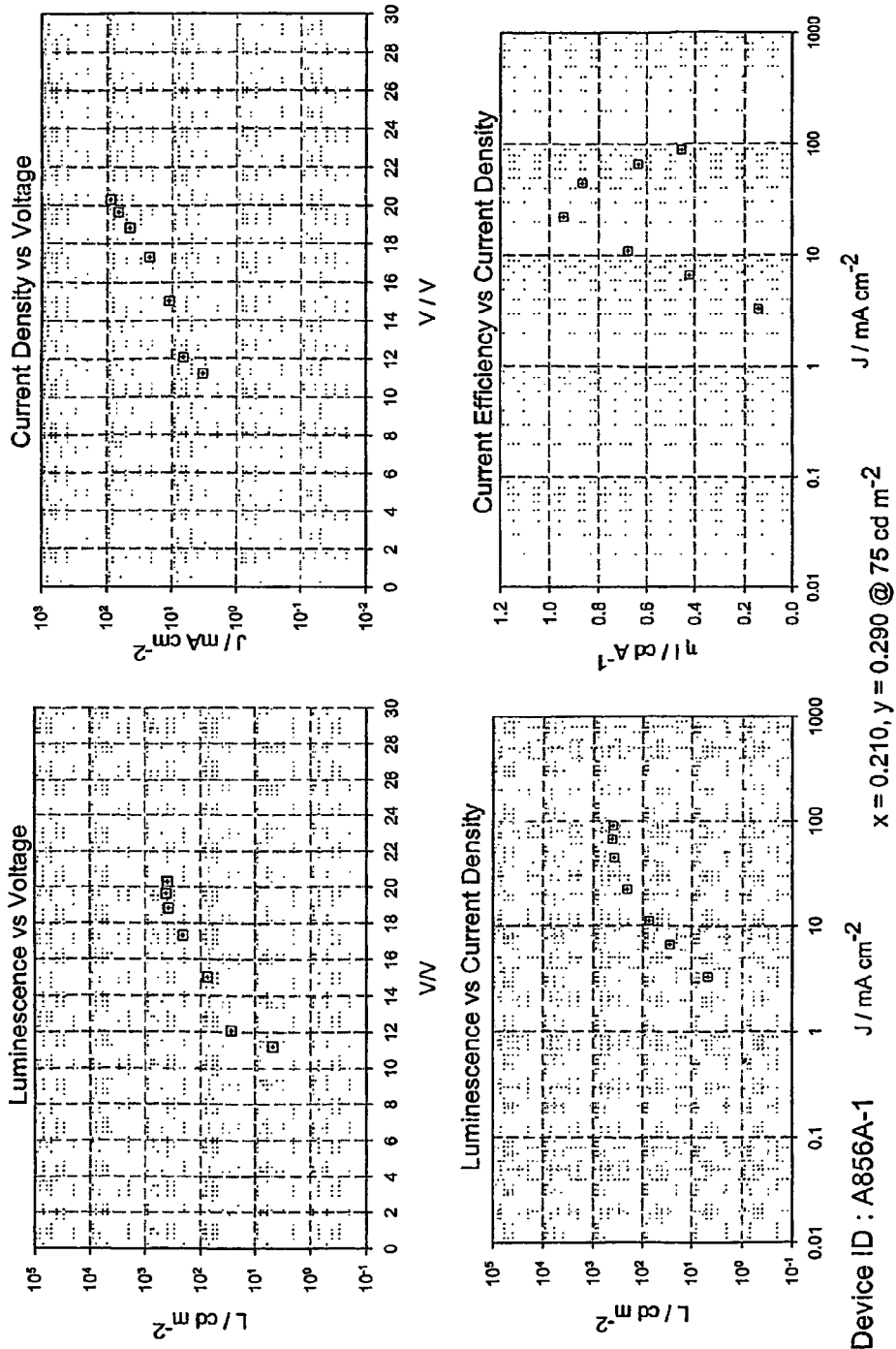

The electroluminescent spectrum and other properties were measured and the results are shown in FIGS. 20 and 21.

Figure 22:
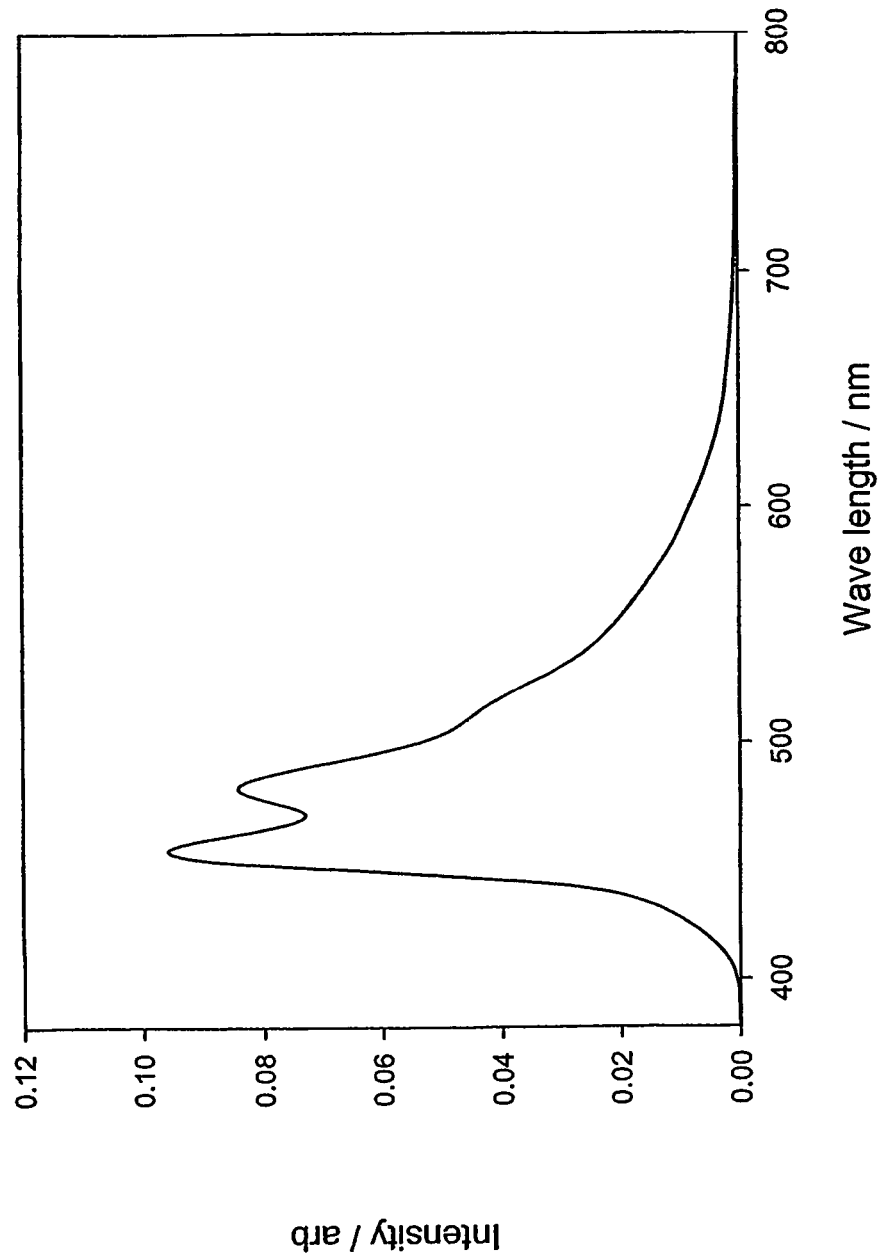
FIGS. 22 and 23 show respectively an electroluminescent spectrum and graphs of luminescence and current density as functions of voltage, and of luminescence and current efficiency as functions of current density for an electroluminescent device according to this invention.
Figure 23:
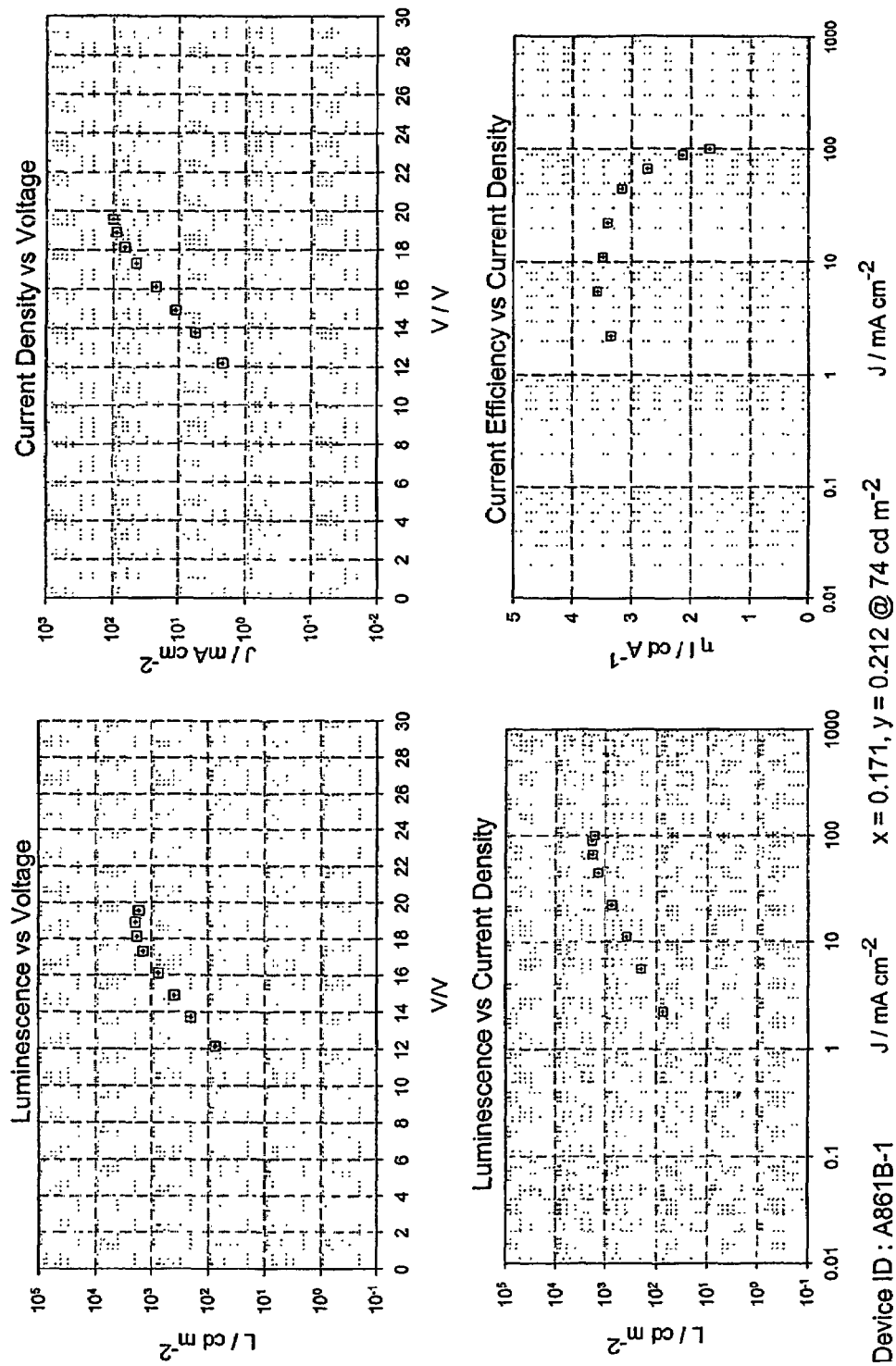

A second electroluminescent device was made with the following layers:

ITO(H)/CuPc (25 nm)/α-NPB (75 nm)/BAlq$_2$ (15
      nm)/Compound C (40 nm)/Zrq$_4$ (10 nm)/LiF (0.5
      nm)/Al In the above structure BAlq$_2$ represents biphenyl aluminium biquinolate (the same as the compound BAlq1 in FIG. 1). The electroluminescent spectrum was measured and the results are shown in FIG. 22. Luminescence and current density were measured as a function of voltage and luminescence and current efficiency were measured as a function of current density with the results shown in FIG. 23.

EXAMPLE 15

An electroluminescent device was made with the following layers:

ITO(H)/CuPc (25 nm)/α-NPB (110 nm)/Compound D
      (40 nm)/BAlq$_2$ (10 nm)/LiF (0.5 nm)/Al in which compound D is of formula:

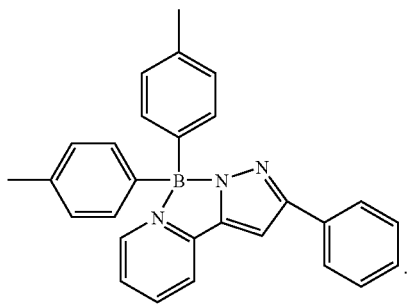

Compound D

Figure 24:
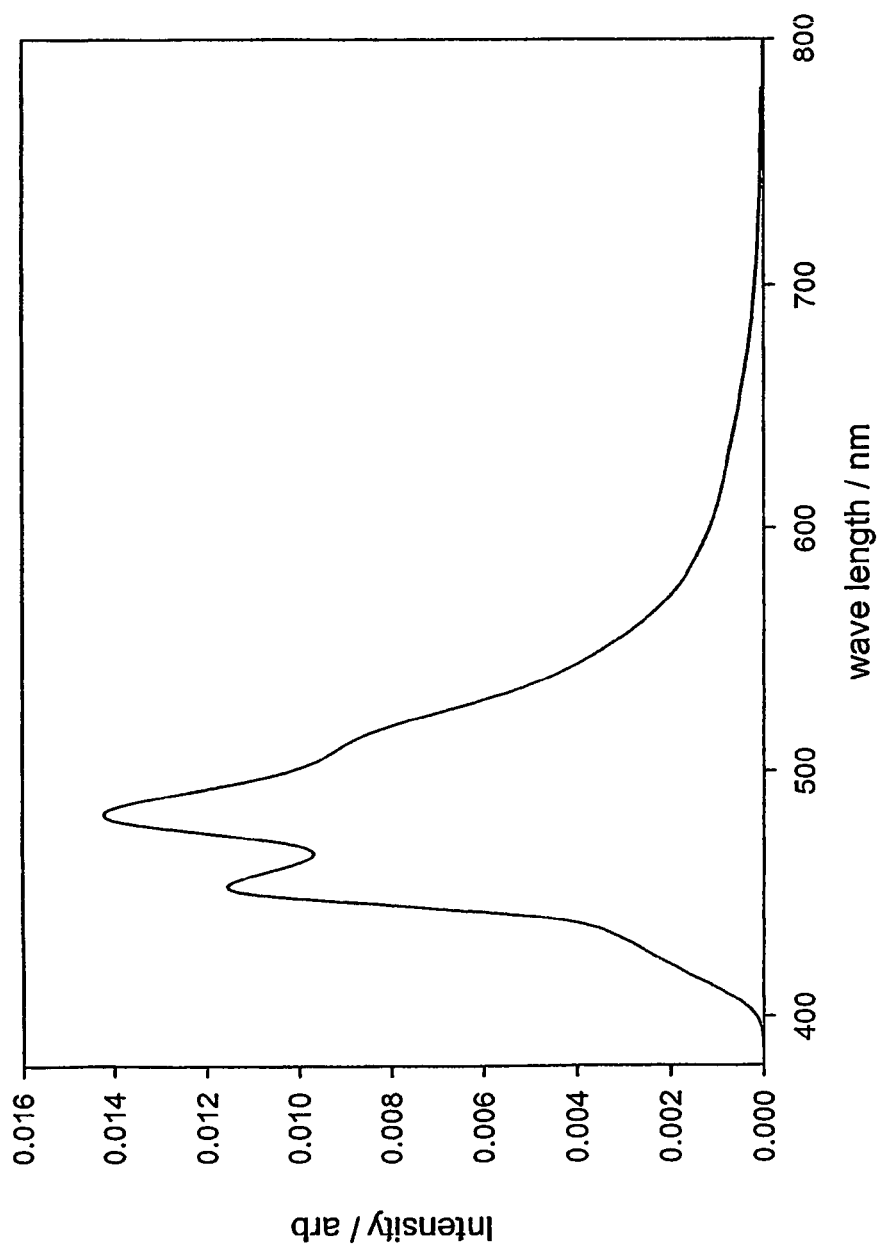
FIGS. 24 and 25 show respectively an electroluminescent spectrum and graphs of luminescence and current density as functions of voltage, and of luminescence and current efficiency as functions of current density for an electroluminescent device according to this invention.
Figure 25:
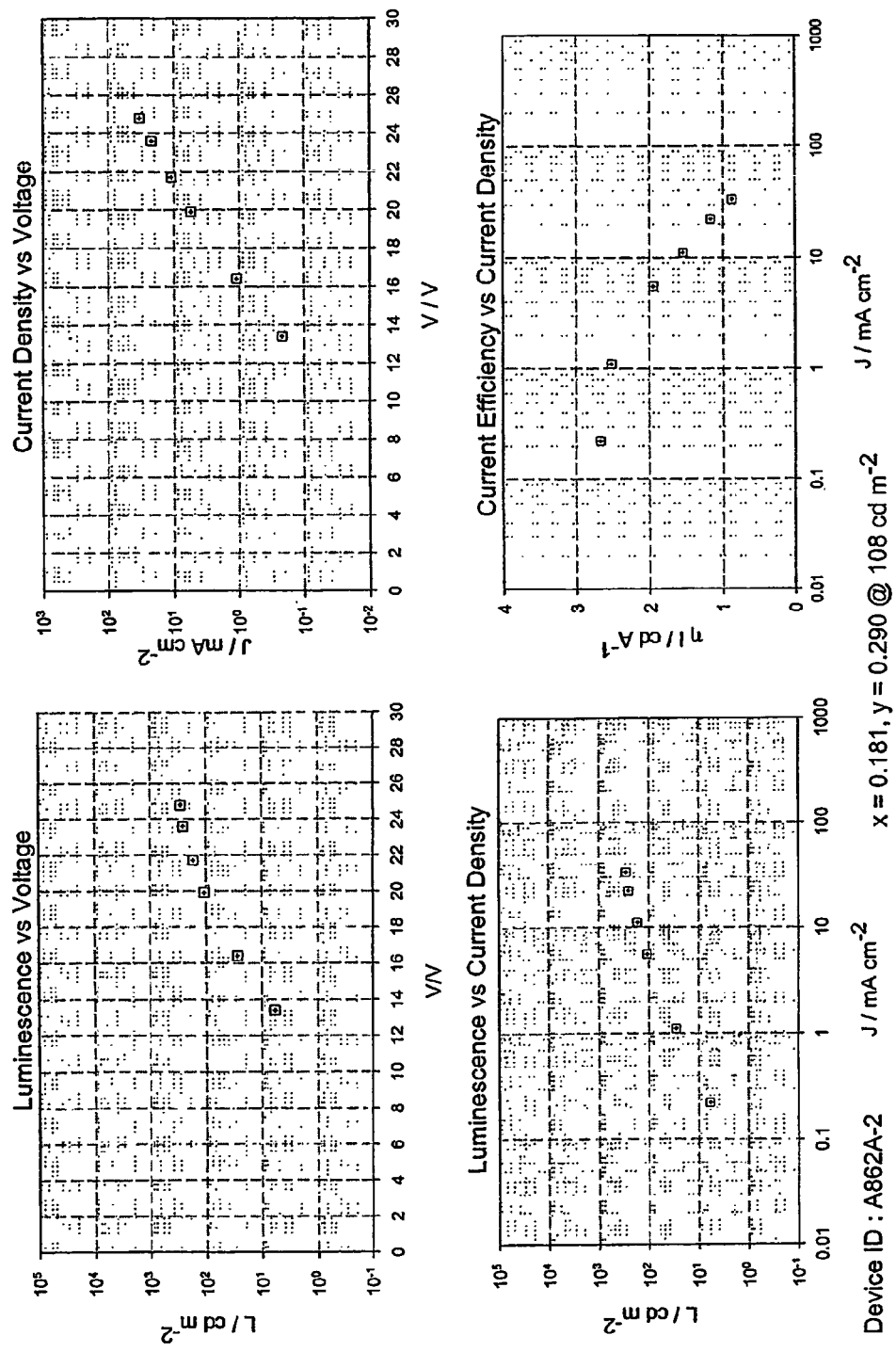

The electroluminescent spectrum was measured and the results are shown in FIG. 24. Luminescence and current density were measured as a function of voltage and luminescence and current efficiency were measured as a function of current density with the results shown in FIG. 25.

EXAMPLE 16

An electroluminescent device was made with the following layers:

ITO(H)/CuPc (25 nm)/α-NPB (60 nm)/Compound E:Perylene (30:0.02 nm)/BAlq$_2$ (10 nm)/LiF (0.5 nm)/Al in which compound E is of formula:

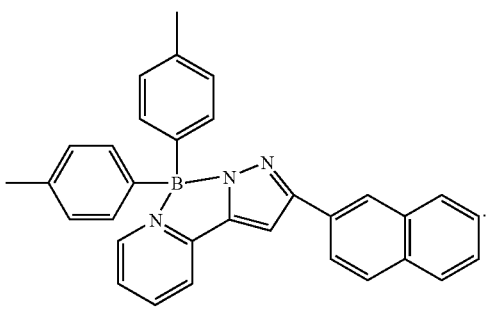

Compound E

Figure 26:
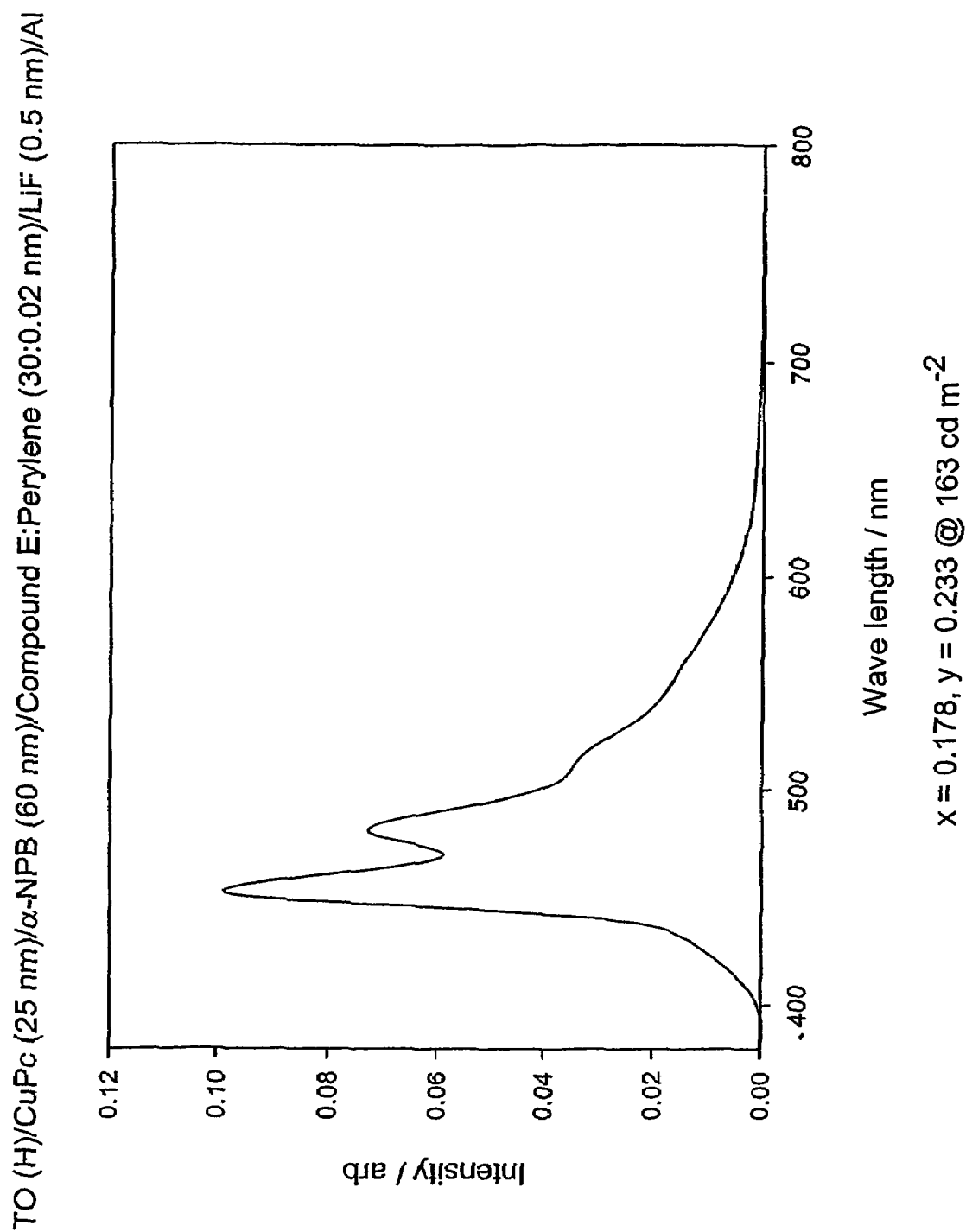
FIGS. 26 and 27 show respectively an electroluminescent spectrum and graphs of luminescence and current density as functions of voltage, and of luminescence and current efficiency as functions of current density for an electroluminescent device according to this invention.
Figure 27:
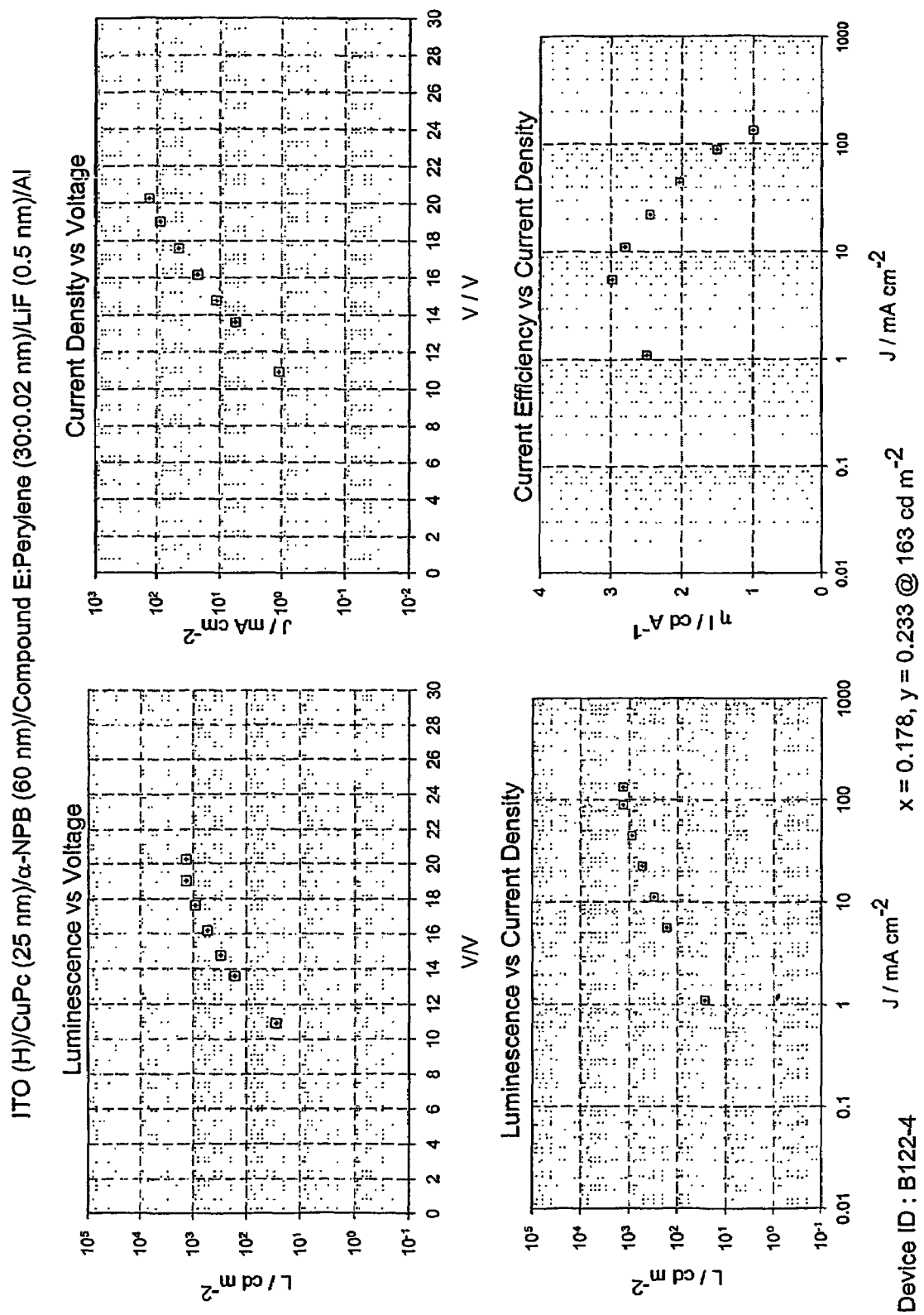

The electroluminescent spectrum was measured and the results are shown in FIG. 26. Luminescence and current density were measured as a function of voltage and luminescence and current efficiency were measured as a function of current density with the results shown in FIG. 27.

The invention claimed is:
1. A boron compound having the general chemical formula (I) as follows

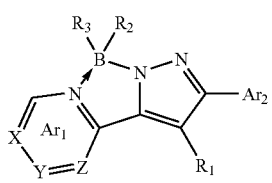

(I)

wherein:
Ar$_1$ represents a chemical group selected from the group consisting of unsubstituted and substituted monocyclic and polycyclic heteroaryl groups having at least a ring nitrogen atom for forming a coordination bond to boron as shown in formula I and, optionally, also including one or more additional ring nitrogen atoms subject to the proviso that such nitrogen atoms do not occur in adjacent positions, X and Z being selected from the group consisting of carbon and nitrogen, and wherein Y is carbon or, optionally, nitrogen if neither of X and Z is nitrogen, the substituents for said substituted heteroaryl groups, if present, being selected from the groups consisting of substituted and unsubstituted hydrocarbyl, substituted and unsubstituted hydrocarbyloxy, fluorocarbon, halo, nitrile, amino alkylamino, dialkylamino and thiophenyl groups;

Ar$_2$ represents a group selected from the group consisting of monocyclic and polycyclic aryl and heteroaryl groups, any of which may optionally be substituted with one or more substituent groups selected from the group consisting of substituted and unsubstituted hydrocarbyl, substituted and unsubstituted hydrocarbyloxy, fluorocarbon, halo, nitrile, amino alkylamino, dialkylamino and thiophenyl groups;

R$_1$ represents hydrogen or a group selected from substituted and unsubstituted hydrocarbyl, halohydrocarbyl and halo groups; and R$_2$ and R$_3$ each independently represent a moiety selected from the group consisting of alkyl, cycloalkyl, cycloalkylalkyl, haloalkyl, halo, monocyclic, polycyclic, aryl, heteroaryl, aralkyl and heteroaralkyl groups, any of which may optionally be substituted with one or more moieties selected from the group consisting of alkyl, cycloalkyl, cycloalkylalkyl, haloalkyl, aryl, aralkyl, alkoxy, aryloxy, halo, nitric, amino, alkylamino and dialkylamino groups.

2. The compound of claim 1, wherein Ar$_1$ is selected from the group consisting of unsubstituted monocyclic and bicyclic heteroaryl groups and monocyclic and bicyclic heteroaryl groups substituted with at least one member selected from the group consisting of C$_1$-C$_4$ alkyl, C$_1$-C$_4$ alkoxy, trifluoromethyl, and fluoro groups; and unsubstituted and substituted pyridyl, pyrimidyl, pyrazinyl, quinolinyl, iso-quinolinyl, quinoxalinyl, and quinazolinyl groups.

3. The compound of claim 1, wherein Ar$_2$ is selected from the group consisting of unsubstituted monocyclic and 2-6 polycyclic aryl groups, and monocyclic and polycyclic aryl groups substituted with one or more members selected from the group consisting of C$_1$-C$_4$ alkyl, C$_1$-C$_4$ alkoxy, trifluoromethyl, fluoro and nitrile groups.

4. The compound of claim 3, further wherein the monocyclic or polycyclic aryl group is selected from the group consisting of phenyl, naphthyl, anthracenyl, phenanthrenyl, pyrenyl and peryleneyl groups.

5. The compound of claim 1, wherein R$_1$ is selected from the group consisting of hydrogen, alkyl, cycloalkyl, cycloalkylalkyl, haloalkyl, monocyclic or polycyclic aryl, heteroaryl, aralkyl, heteroaralkyl, C$_1$-C$_4$ alkyl, trifluoromethyl, and fluoro groups.

6. The compound of claim 1, wherein R$_2$ and R$_3$ are selected from the group consisting of phenyl and 4-substituted phenyl groups.

7. The compound of claim 6, wherein the substituent in the 4-position is selected from the group consisting of C$_1$-C$_4$ alkyl, trifluoromethyl, C$_1$-C$_4$ alkoxy and fluoro groups.

8. An electroluminescent device comprising in combination a first electrode, a layer of an electroluminescent material consisting essentially of the boron compound as claimed in claim 1, and a second electrode.

9. The device of claim 8, further comprising a layer of a hole transporting material located between the first electrode, which functions as the anode, and the layer of the electroluminescent material.

10. An electroluminescent device according to claim 9, wherein the hole transporting material is a film of a polymer selected from the group consisting of poly(vinylcarbazole), N,N'-diphenyl-N,N'-bis (3-methylphenyl)-1,1'-biphenyl-4,4'-diamine (TPD), polyaniline, substituted polyanilines, polythiophenes, substituted polythiophenes, polysilanes and substituted polysilanes, a polymer of a cyclic aromatic compound, poly(p-phenylenevinylene)-PPV and copolymers thereof, PPV, poly(2,5 dialkoxyphenylene vinylene), poly(2-methoxy-5-(2-methoxypentyloxy-1,4-phenylene vinylene), poly(2-methoxypentyloxy)-1,4-phenylenevmylene), poly(2-methoxy-5-(2-dodecyloxy-1,4-phenylenevinylene), other poly(2,5 dialkoxyphenylenevinylenes) with at least one of the alkoxy groups being a long chain solubilizing alkoxy group, poly fluorenes and oligofluorenes, polyphyenylenes, oligophenylenes, polyanthracenes, oligo anthracenes, polythiophenes and oligothiophenes.

11. An electroluminescent device according to claim 8, further comprising a layer of an electron transmitting material located between the electroluminescent material layer and the second electrode.

12. An electroluminescent device according to claim 11, wherein the electron transmitting material is selected from the group consisting of metal quinolates, cyano anthracenes, 9,10 dicyano anthracene, and polystyrene sulphonates.

13. An electroluminescent device according to claim 11, wherein the electron transmitting material is an aluminum quinolate or lithium quinolate.

14. The device of claim 11, wherein the electron transmitting material has the general chemical formula $Mx(DBM)_n$ where Mx is a metal, DBM is dibenzoyl methane, and n is the valency of Mx, or wherein a Schiff base is used in place of the DBM.

15. An electroluminescent device comprising a first electrode which functions as an anode, a layer of a hole transporting material, a layer of an electroluminescent material consisting essentially of the boron compound as claimed in claim 1, a layer of an electron transmitting material, and a second electrode which functions as a cathode.

16. An electroluminescent device according to claim 15, further wherein the hole transmitting material and the electroluminescent material are mixed in a proportion of about 5 to 95% of the hole transmitting material to about 95 to 5% of the electroluminescent compound to form one layer.

17. An electroluminescent device according to claim 15, wherein the electron transmitting material and the electroluminescent material are mixed in a proportion of about 5 to 95% of the electron transmitting material to about 95 to 5% of the electroluminescent material to form one layer.

18. An electroluminescent device according to claim 15, wherein the second electrode consists essentially of a material selected from the group consisting of aluminum, calcium, lithium and silver/magnesium alloys.

19. The device of claim 15, wherein the second electrode consists essentially of a material selected from the group consisting of metals having a metal fluoride layer formed thereon.

20. The device of claim 19, wherein the metal fluoride is a lithium fluoride or rare earth fluoride.

* * * * *